(12) United States Patent
Schneider et al.

(10) Patent No.: US 9,452,099 B2
(45) Date of Patent: Sep. 27, 2016

(54) CLEANING APPARATUS FOR CLEANING ARTICLES

(71) Applicant: MEIKO Maschinenbau GmbH & Co. KG, Offenburg (DE)

(72) Inventors: Vera Schneider, Offenburg (DE); Thomas Näger, Offenburg (DE); Thomas Peukert, Bühl (DE); Hans-Josef Rauber, Oberhamersbach (DE); Ingo Wiegand, Bühlertal (DE)

(73) Assignee: MEIKO Maschinenbau GmbH & Co. KG, Offenburg (DE)

( * ) Notice: Subject to any disclaimer, the term of this patent is extended or adjusted under 35 U.S.C. 154(b) by 397 days.

(21) Appl. No.: 13/960,444

(22) Filed: Aug. 6, 2013

(65) Prior Publication Data
US 2013/0319460 A1   Dec. 5, 2013

Related U.S. Application Data

(63) Continuation of application No. PCT/EP2012/051643, filed on Feb. 1, 2012.

(30) Foreign Application Priority Data

Feb. 8, 2011   (DE) .................. 10 2011 003 782

(51) Int. Cl.
  *B08B 3/00*    (2006.01)
  *A61G 9/02*    (2006.01)
  *A47L 15/00*   (2006.01)
  (Continued)

(52) U.S. Cl.
  CPC ............ *A61G 9/02* (2013.01); *A47L 15/0015* (2013.01); *A47L 15/0078* (2013.01); *A47L 15/241* (2013.01); *A47L 15/4236* (2013.01); *A61L 2/14* (2013.01); *A47L 15/4223* (2013.01); *A47L 2601/20* (2013.01); *A61L 2202/17* (2013.01)

(58) Field of Classification Search
  None
  See application file for complete search history.

(56) References Cited

U.S. PATENT DOCUMENTS

| 5,871,692 A | 2/1999 | Haire et al. |
| 6,187,266 B1 | 2/2001 | Lin et al. |

(Continued)

FOREIGN PATENT DOCUMENTS

| CN | 2296170 Y | 11/1998 |
| CN | 2333398 Y | 8/1999 |

(Continued)

OTHER PUBLICATIONS

English Translation of International Preliminary Report on Patentability, PCT/EP2012/051643, Aug. 8, 2013.

(Continued)

*Primary Examiner* — Eric Golightly
(74) *Attorney, Agent, or Firm* — Bose McKinney & Evans LLP

(57) ABSTRACT

A cleaning apparatus for cleaning articles is proposed. The cleaning apparatus comprises at least one cleaning chamber for receiving the articles. The cleaning apparatus comprises, in the cleaning chamber, at least one fluid source for subjecting the articles to the action of at least one cleaning fluid. The cleaning apparatus furthermore comprises at least one plasma source, which is designed to ignite at least one plasma in at least one gas and to generate at least one reactive gas. The cleaning apparatus is designed to bring the reactive gas into contact with the articles, at least in part.

22 Claims, 6 Drawing Sheets

(51) Int. Cl.
*A47L 15/24* (2006.01)
*A47L 15/42* (2006.01)
*A61L 2/14* (2006.01)

(56) References Cited

U.S. PATENT DOCUMENTS

| | | |
|---|---|---|
| 7,695,568 B2 | 4/2010 | Gaus |
| 2004/0206133 A1 | 10/2004 | Woo et al. |
| 2007/0104608 A1 | 5/2007 | Gaus et al. |
| 2008/0236631 A1 | 10/2008 | Lin et al. |
| 2009/0183753 A1 | 7/2009 | Maennle et al. |
| 2010/0132735 A1 | 6/2010 | Gaus et al. |
| 2010/0226821 A1 | 9/2010 | Ricciardi et al. |
| 2012/0111359 A1 | 5/2012 | Mueller et al. |

FOREIGN PATENT DOCUMENTS

| | | |
|---|---|---|
| CN | 101124000 A | 2/2008 |
| DE | 198 58 344 A1 | 6/1999 |
| DE | 10 2006 050 876 A1 | 4/2008 |
| EP | 1 765 044 A1 | 3/2007 |
| EP | 1 993 329 A1 | 11/2008 |
| EP | 2 160 081 A1 | 3/2010 |
| EP | 2 170 022 A1 | 3/2010 |
| EP | 2 387 907 A1 | 11/2011 |
| FR | 2 827 777 A1 | 1/2003 |
| JP | 2005 103376 A | 4/2005 |
| JP | 2010 194060 A | 9/2010 |
| JP | 2010 220741 A | 10/2010 |
| NL | 1033408 C2 | 8/2008 |
| WO | WO 98/30249 A2 | 7/1998 |
| WO | WO 2005/018407 A2 | 3/2005 |
| WO | WO 2008/145217 A1 | 12/2008 |
| WO | WO 2010/034451 A1 | 4/2010 |
| WO | WO 2010/094304 A1 | 8/2010 |
| WO | WO 2010/094307 A1 | 8/2010 |
| WO | WO 2011/110343 A1 | 9/2011 |
| WO | WO 2011/141263 A1 | 11/2011 |

OTHER PUBLICATIONS

Verfahrenstechnik Jan. 2, 2010, Seite 12 not in English. considered to the extent it could be understood.

G. E. Morfill et al.: Nosocomial infections—A new approach towards preventive medicine using plasmas, New Journal of Physics 11 (2009) 115019.

M. Vogel: Hineinhalten statt waschen—Ein Plasmaspender vereinfacht die Desinfektion der Hände, Physik Journal, Jan. 2010, Seite 16 not in English.

CLEANING APPARATUS FOR CLEANING ARTICLES

RELATED APPLICATIONS

This application is a continuation of PCT/EP2012/051643, filed Feb. 1, 2012, which claims priority to DE 10 2011 003 782.9, filed Feb. 8, 2011, both of which are hereby incorporated by reference in their entireties.

BACKGROUND

The invention relates to a cleaning apparatus and to a method for cleaning articles. The invention further relates to a use of a reactive gas, generated by a plasma source from at least one gas, for cleaning articles in a cleaning apparatus. Cleaning apparatuses, methods, and uses of this type are used in particular in the field of rinsing technology in order to clean articles, in the form of dinnerware, such as plates, cups, glasses, bowls, serving dishes, cutlery, trays and other objects that are used for the preparation and/or presentation and/or storage of food. Cleaning apparatuses of this type are used, for example, in large professional kitchens, for example, in large professional kitchens of company canteens, hospitals, care homes, government agencies, schools, or universities. In another embodiment, the cleaning apparatus, the method, and the use can also be used in the field of the cleaning of articles in the form of care utensils, such as pans, bedpans, urine bottles or similar care utensils, which come into contact with human or animal excretions. In a further possible embodiment, the cleaning apparatus, the method and the use can be used, for example, in order to clean other types of articles, for example, pieces of equipment belonging to personal protective equipment of rescue workers or divers, such as protective breathing masks, breathing masks, oxygen cylinders, diving regulators, snorkels, masks or similar pieces of equipment. In a further possible embodiment, the cleaning apparatus, the method, and the use can be used, for example, in order to clean food, in particular fruit and vegetables and particularly preferably salad. Other fields of use are conceivable however in principle.

A large number of cleaning apparatuses for cleaning different types of articles are known from the prior art. For example, cleaning apparatuses of this type in the form of dishwashers, in particular for commercial use, are known from DE 10 2004 056 052 A1. Cleaning apparatuses in the form of what are known as cleaning and disinfection units, by means of which care utensils for care needs can be cleaned, are likewise described. Dishwashers, for example, in particular for commercial use, are known from DE 10 2006 050 876 A1. Dishwashers which are designed as pass-through dishwashers and in particular as multi-tank dishwashers are likewise known from DE 10 2006 039 434 A1. Further types of cleaning apparatuses in the form of cleaning and disinfection units are known, for example, from DE 103 48 344 B4 or from EP 1 824 373 B1.

It also known from the above-described prior art that increasing importance is ascribed to the guarantee of disinfection of the articles. In particular in hygiene-critical areas, such as hospitals or nursing care facilities, but also in areas of a communal feeding space, in particular in large professional kitchens, sanitization of the articles must be guaranteed.

Disinfection processes in cleaning apparatuses, for example, in dishwashers or cleaning and disinfection machines, are generally known from the prior art as thermal disinfection steps. Thermal disinfection of this type is generally performed by means of hot aqueous liquids and/or by means of steam. The disinfection medium used here is either introduced in an undirected manner into a cleaning chamber and delivers its heat content to the articles, or the medium is sprayed directly onto the articles, wherein a heat content is likewise delivered. This is described, for example, in the above-mentioned documents DE 103 48 344 B4 and EP 1 824 373 B1 and also in DE 10 2004 056 052 A1. Thermal disinfection processes of this type are likewise described in DE 10 2004 056 052 A1 for dishwashers, or, for pass-through dishwashers, in DE 10 2006 039 434 A1, for example.

Furthermore, disinfection methods that are performed using chemical agents, and also combinations of thermal and chemical disinfection methods are also known and are widespread. A method and an apparatus with which a disinfection effect is achieved by a combined use of UV light and/or by the use of ozone generated by a UV radiator, are also known from DE 10 2006 050 876 A1.

The apparatuses and methods known from the prior art present a series of technical challenges and disadvantages. A disadvantage in particular of the thermal disinfection methods lies in a relatively high use of energy to heat the media used for the disinfection. For example, in many cases, liquid media are heated to 90° C., for example. Alternatively or additionally, steam has to be produced as a disinfection medium in many cases. An increased use of energy is generally also accompanied by a relatively long process duration. A further disadvantage lies in the fact that, at the end of the disinfection process, the articles are generally very hot and first have to be cooled again, thus eliminating the risk that an operator will injure himself by touching the hot articles.

By contrast, chemical disinfection methods function using generally aggressive chemicals. These can cause ecological problems or can pose health risks during use and/or in the event of disposal. In addition, in many chemical disinfection methods used on dinnerware and similar objects that are used for the preparation, presentation or storage of food, the articles may be tainted by an unpleasant taste. In particular when cleaning drinking glasses, chemical disinfectants, for example, in many cases produce an adhering chlorine taste and/or chlorine smell, which is undesirable.

Furthermore, plasma sources for disinfection purposes are known in particular from the medical field. For example, an electrode arrangement for producing a non-thermal plasma is known from WO 2010/094304 A1. This electrode arrangement comprises a layer-shaped first electrode produced from an electrically conductive material, and a layer-shaped second electrode produced from an electrically conductive material, wherein the second electrode is electrically insulated from the first electrode. Furthermore, a dielectric barrier is arranged between the first electrode and the second electrode, such that the non-thermal plasma is generated by a dielectric barrier discharge. At least one of the electrodes comprises a plurality of perforations, which are distributed over the electrode. EP 2 170 022 A1 and WO 2010/034451 A1 describe an apparatus for applying a plasma to human skin, for example. WO 2010/094307 A1 describes an apparatus for the plasma treatment of body parts, and EP 2 160 081 A1 describes an apparatus for application of a plasma, wherein additional substances are added to the plasma in order to influence the effect. Further embodiments of plasma sources are described in EP 1 993 329 A1 and in EP 1 765 044 A1.

A method for textile cleaning and textile disinfection by means of plasma is described in DE 102007037984 A1. A plasma source for sterilizing PET bottles is also known from the publication Verfahrenstechnik (Process Engineering) 1-2/2010, page 12. In this case a pin is used, which generates a plasma jet. For example, plastic films and/or other types of packagings can be treated and thus sterilized by means of this plasma jet.

SUMMARY

This disclosure proposes a cleaning apparatus and a method for cleaning articles which at least largely avoid the disadvantages of known apparatuses and methods. In particular, disinfection of the articles that is gentle for the articles, the operator and the environment and that can be implemented cost-effectively and without relatively high energy expenditure is to be enabled.

In a first aspect of this disclosure, a cleaning apparatus for cleaning articles is proposed. Within the scope of this disclosure, a cleaning apparatus is to be understood to mean an apparatus that is designed to remove, at least to a large extent, contamination contained in the articles and/or contaminations adhering to the articles, and preferably also to disinfect the articles, that is to say to kill at least a large percentage, for example, at least 99%, preferably at least 99.9%, or even at least 99.999% or more, of microbial contaminations adhering to the articles.

As mentioned above, the articles can be selected in particular from the group consisting of: dinnerware, care utensils, food, and personal protective equipment. Other articles can also be cleaned however in principle.

The cleaning apparatus may in particular comprise at least one receptacle and/or at least one holder for fixing and/or receiving the articles, in particular, at least one rack, at least one pocket, or at least one other type of holder.

As mentioned above, the term "dinnerware" is broad and, for example, can include the above-specified objects, but in principle can include all types of objects that are designed or that can be used for the preparation, presentation or storage of food. The term "care utensils" is also broad and in particular can include objects selected from the group consisting of pans, bedpans, urine bottles and wash bowls.

The term "personal protective equipment" is likewise broad and in principle can include any objects that are used for personal protection or for survivability in hostile or aggressive environments, for example, rubber shoes that are used in operating theatres, or objects selected from the group consisting of breathing masks, protective breathing masks, breathing tubes, protective goggles, diving regulators, snorkels, mouthpieces, and protective clothing.

The term "food" can in principle include any plant and/or animal and/or artificial products in liquid and/or solid form that are suitable for consumption by a human or an animal. In particular, the term "food" may include fruit or vegetables and particularly preferably salad. The cleaning apparatus may therefore be designed in particular completely or in part as a vegetable washing machine, for example.

The cleaning apparatus comprises at least one cleaning chamber for receiving the articles. Here, a cleaning chamber is to be understood to mean a space which is closed by a housing and within which the articles can be received at least temporarily and can be subjected to a cleaning method. For example, the cleaning chamber may be enclosed completely or in part by a housing, in particular a metal housing. The cleaning chamber may be completely closed, wherein a pressure equalization with a surrounding environment can be implemented, for example, wherein articles can be introduced and discharged, however, through at least one closable opening, for example, such as a door. Alternatively or additionally, the cleaning chamber, as will be discussed in greater detail below, can also be designed, however, as a chamber that is open on one or more sides, for example, in the form of a cleaning tunnel, into which the articles are inserted on one side, wherein said articles can be discharged from the cleaning chamber on an opposite side, for example. Various other embodiments are possible. The cleaning chamber can be designed to maintain a normal pressure and/or an ambient pressure inside the cleaning chamber, wherein, for example, a pressure equalization between an interior of the cleaning chamber and a surrounding environment is implemented. Alternatively or additionally, however, a pressure deviating from an ambient pressure may also prevail inside the cleaning chamber in one or more program steps, for example, a negative pressure or an overpressure, and/or a composition of an atmosphere deviating from a surrounding environment may prevail inside the cleaning chamber. Various embodiments are possible.

The cleaning apparatus comprises, in the cleaning chamber, at least one fluid source for subjecting the articles to the action of at least one cleaning fluid. The cleaning fluid may be or may comprise a cleaning liquid in particular. Alternatively or additionally, other liquid and/or gaseous media can also be used, however, as cleaning fluid. In particular, the cleaning fluid may comprise at least one aqueous cleaning fluid, where appropriate with addition of additives and/or auxiliary agents, for example, at least one detergent solution and/or one final rinse solution and/or one disinfectant. Various embodiments are known in principle from the field of rinsing technology and/or cleaning technology and can likewise be used within the scope of this disclosure. The at least one fluid source may comprise, for example, at least one jet and/or at least one jet system, by means of which the cleaning fluid is sprayed, blasted, dropped, poured or applied in another way onto the articles. This application can be performed in a pressureless manner or also by means of an overpressure.

To solve the above-described problem, it is proposed to design the cleaning apparatus in such a way that it also comprises at least one plasma source. The plasma source is designed to ignite at least one plasma in at least one gas and to generate at least one reactive gas. The cleaning apparatus is designed to bring the reactive gas into contact with the articles, at least in part, in particular inside the cleaning chamber and/or inside at least one disinfection chamber.

A concept of this disclosure therefore lies in using at least one plasma source for disinfection. In particular, plasma sources that can be easily handled and can generate plasmas at room temperature and/or at comparatively low temperatures have recently been developed. Plasmas of this type are often referred to as "cold plasmas". In particular, a cold plasma may have temperatures of no more than 100° C., in particular of no more than 80° C., and, for example, of no more than 60° C. or even no more than 40° C. Accordingly, within the scope of this disclosure, a "plasma source" is to be understood to mean an apparatus that is designed to ignite at least one plasma. For example, as will be discussed in greater detail below, the plasma source for this purpose may comprise at least one, preferably at least two, electrodes, for example, as will likewise be discussed in greater detail below, at least one electrode having a continuous surface and at least one electrode having a plurality of openings, for example, a grid electrode. Other types of plasma sources are also known in principle however, for example, high-voltage sources, which can generate a plasma with use of a high voltage. With regard to possible plasma sources, reference can be made by way of example to the above-mentioned prior art. Other plasma sources can also be used, however, in principle.

The at least one gas in which the plasma is ignited may be a gas provided specifically for the ignition of the plasma, but in principle may be an oxygen-containing gas, in particular, and preferably, air. This gas can be provided in the cleaning chamber or outside the cleaning chamber, wherein, in the latter case, the generated reactive gas can be transferred into the cleaning chamber, for example. Other embodiments are also possible, however, in principle. In particular, the gas can be moist air, in particular air having an air humidity of at least 80%, preferably at least 90%, in particular at least 95%, or even at least 98%, or even 100%, for example, in the form of mist. Either instead of or additionally to a use of dry or moist air as gas in which the plasma is ignited, other gases can also be used, or components that influence the ignition of the plasma and/or the composition of the reactive gas can be added to the air, for example, purposefully.

A "reactive gas" is to be understood generally to mean a gas that has a physical and/or chemical and/or biological effect, for example, a disinfecting effect. The reactive gas is gaseous, but in principle may also comprise one or more liquid components, for example, in droplet form or also in the form of an aerosol. In particular, as will be discussed in greater detail below, the reactive gas may comprise at least one reactive component, preferably selected from: ozone, a reactive oxygen compound, a reactive nitrogen compound, atomic oxygen, atomic nitrogen, or hydrogen peroxide. Other types of reactive gases are also possible, however, in principle. Alternatively or additionally, as will be discussed in greater detail below, the reactive gas may comprise at least one plasma, in particular, the plasma generated by the plasma source and/or part thereof, preferably at least one cold plasma according to the above definition. Within the scope of this disclosure, a "plasma" is to be understood generally to mean a gas that is composed in part or completely of free charge carriers, in particular ions and/or electrons. In particular, the plasma may generally be a mixture of neutral and charged particles, for example, atoms and/or molecules. A ratio between charged particles and uncharged particles in the plasma, for example, a ratio between charged molecules or ions and uncharged molecules or ions, may be from 10-8-10-11, in particular 10-9-10-10, for example.

In particular, the reactive gas can be brought into contact with the articles at least in part in such a way that at least a surface of the articles is brought fully or partially into contact with the reactive gas, and in particular in such a way that the reactive gas washes over said surface. As discussed above, this contacting process may take place inside the cleaning chamber itself, in which the articles are also subjected to the action of the at least one cleaning fluid, and/or inside at least one separate disinfection chamber. Various embodiments are possible. The plasma can be generated inside the cleaning chamber and/or inside the disinfection chamber itself or in a separate space, for example, a separate plasma source, wherein the reactive gas generated by the plasma is then preferably introduced into the cleaning chamber and/or the disinfection chamber, for example, by being drawn in and/or blown in.

A concept of this disclosure therefore lies in causing a disinfecting effect in the cleaning apparatus by use of a reactive gas generated by a plasma. Plasma sources of this type and reactive gases of this type generated by plasmas are known in principle from the prior art. For example, plasma sources by means of which "cold plasmas" can be generated are described in G. E. Morfill et al.: Nosocomial infections—A new approach towards preventive medicine using plasmas, New Journal of Physics 11 (2009) 115019. These plasma sources, which can also be used in the scope of this disclosure, may, for example, comprise one or more electrodes, for example, a first electrode designed as an electrode having a continuous surface, in particular as a copper electrode, and a second electrode designed as a mesh electrode, for example. A sinusoidal A.C. voltage can be applied to these electrodes, wherein a plasma is ignited. This plasma is generally characterized by a low temperature, for example, room temperature, and reactive gas components form, in particular reactive oxygen compounds and reactive nitrogen compounds as well as atomic oxygen, nitrogen and $H_2O_2$ by interaction with steam. Furthermore, a disinfecting effect of plasma sources of this type is described in the above publication and also in M. Vogel: Hineinhalten statt waschen—Ein Plasmaspender vereinfacht die Desinfektion der Hände (hand placement instead of hand washing—a plasma donor simplifies disinfection of the hands), Physik Journal, January 2010, page 16. In accordance with this disclosure, it is therefore proposed to use one or more plasma sources, for example, as described in the aforementioned prior art, also in the cleaning apparatus according to this disclosure.

The cleaning apparatus can be designed in particular to bring the reactive gas into contact, inside the cleaning chamber, with the articles at least in part. Alternatively or additionally, the contacting may also occur outside the cleaning chamber, however, in particular in a separate disinfection chamber, which, for example, may be connected to the cleaning chamber and/or may be arranged in a common housing with the cleaning chamber and/or may be associated with the cleaning chamber in terms of a procedure.

As described above, the cleaning apparatus can be designed for cleaning various types of articles. In particular, the cleaning apparatus may comprise a one-chamber cleaning apparatus having exactly one cleaning chamber. For example, in order to insert and/or remove the articles, the cleaning chamber can be opened and/or closed, for example, by at least one hatch and/or at least one lid and/or at least one slide and/or at least one hood.

The cleaning apparatus may in particular comprise at least one controller. The controller can be designed in particular to control at least one cleaning program in the cleaning apparatus. For example, the controller may be a central or a decentralized controller. The controller may, for example, comprise at least one data processing apparatus and/or at least one program electronics unit in order to control the at least one cleaning program. The articles can be acted on by the at least one cleaning fluid in at least one cleaning program step. In at least one disinfection step, which, for example, can be separate from the at least one cleaning program step, for example, can be arranged downstream thereof, the articles can be acted on by the reactive gas, preferably once the cleaning program step has been carried out. For example, one or more cleaning program steps in which the articles are acted on by the cleaning fluid, for example, with different purity levels and/or different compositions of the cleaning fluid, can thus be carried out. The at least one disinfection step may then be carried out, for example. Another order of the program steps is also conceivable in principle, for example, in which at least one disinfection step is carried out before at least one cleaning program step. In addition, the cleaning program may comprise one or more further program steps, for example, one or more drying steps. The at least one disinfection step can be carried out before, during, or after the drying step.

The one-chamber cleaning apparatus may comprise or may be in particular at least one one-chamber dishwasher. In particular, the one-chamber dishwasher may be a commercial one-chamber dishwasher comprising at least one wash tank and at least one after rinse tank formed separately from the wash tank. This after rinse tank may comprise in particular at least one boiler. Alternatively or additionally, at least one tankless water heater may also be provided however. In contrast to conventional dishwashers suitable for domestic use, an after rinse fluid can already be prepared in the after rinse tank parallel to the process of subjecting the articles to the action of cleaning fluid from the wash tank. For example, fresh water can be prepared, for example, fresh water can be heated to a temperature of at least 60° C., in particular at least 70° C., preferably at least 80° C., and particularly preferably at least 85° C., optionally, with addition of one or more additives, such as rinse aids or other additives. The wash tank can be integrated fully or partially into the cleaning chamber, for example, in a base region of the cleaning chamber. In particular, the one-chamber dishwasher can be designed as a frontloader dishwasher or as a hood-type dishwasher or as a toploader dishwasher. The one-chamber dishwasher can be designed for cleaning dinnerware, but can also be used in principle however for cleaning personal protective equipment. The cleaning apparatus in this or in other embodiments of this disclosure may comprise in particular at least one holder for receiving the articles, for example, at least one rack, in particular at least one dish rack. Other embodiments are also possible however in principle.

Alternatively or additionally to the embodiment of the cleaning apparatus or part thereof as a one-chamber dishwasher, the one-chamber cleaning apparatus may also comprise at least one cleaning and disinfection unit for cleaning care utensils, in particular, for cleaning pans, bedpans, urine bottles, wash bowls, or similar care utensils that are suitable for receiving liquid and/or solid waste, in particular human excretions, of at least 100 ml, preferably at least 500 ml, or even at least 1,000 ml. A "cleaning and disinfection unit" is to be understood generally to mean an apparatus that can clean, by means of a fluid, and disinfect the articles. The cleaning and disinfection unit preferably comprises at least one drain for disposal of excretions contained in the care utensils, for example, with liquid volumes of at least 100 ml, preferably at least 500 ml, or even at least 1,000 ml. For example, a drain with a diameter or equivalent diameter or at least 30 mm, preferably at least 50 mm, particular preferably at least 75 mm, or even at least 100 mm can be provided. The drain can be designed in particular with an odor trap, preferably at least one siphon bend. In particular, at least one liquid volume can be provided as an odor trap in said odor trap. The cleaning apparatus can be designed in particular to convey the reactive gas, preferably once the reactive gas has acted on the articles, from the cleaning chamber and into the drain, in particular by means of a forced displacement from the cleaning chamber, for example, by steam and/or compressed air and/or another compressed gas, in particular into the drain after an odor trap, preferably after a siphon bend. The reactive gas can thus be conveyed from the cleaning chamber in a manner in which a siphon bend is bypassed, for example.

Alternatively to the embodiment of the cleaning apparatus or part thereof as a one-chamber dishwasher, the cleaning apparatus, in particular the one-chamber cleaning apparatus, may also be formed completely or in part as a cleaning apparatus for cleaning at least one food. In particular, the cleaning apparatus can be designed completely or in part as a cleaning and disinfection unit for cleaning vegetables, fruit, salad, or the like. For example, the cleaning apparatus may comprise at least one receptacle for food.

In a further embodiment of this disclosure, it is thus preferable if the cleaning apparatus is designed completely or in part as a cleaning apparatus for food, in particular for vegetables and/or fruit, in particular for salad, berries, tubers, or similar foods. Other types of food can also be cleaned in principle.

The cleaning apparatus may in particular comprise at least one controller, wherein the controller is designed to control at least one cleaning program in the cleaning apparatus. With regard to possible embodiments of the controller, reference can be made to the above description or to the following description of controllers of this type. In particular, the controller may comprise at least one data processing apparatus. The cleaning program is to be designed in such a way that the food is acted on by the cleaning fluid in at least one cleaning program step. In at least one disinfection step, which is preferably at least partly separate from the cleaning program step, the food is to be acted on by the reactive gas, preferably once the cleaning program step has been carried out.

The cleaning apparatus may in particular comprise at least one lid, in particular at least one hinged lid for loading the cleaning apparatus from above with the food. The at least one plasma source, or, if a plurality of plasma sources are provided, preferably at least one of these plasma sources, can be arranged in particular at least in part in the lid. For example, at least one electrode arrangement of the plasma source can be arranged completely or partially in the lid. Other embodiments of the plasma source are also possible however either alternatively or additionally, for example, in accordance with one or more of the embodiments described previously or hereinafter.

The cleaning apparatus may in particular comprise at least one receptacle for at least one food constituting articles. This receptacle, for example, may be one or more receiving racks, for example, a round receiving rack, which, for example, is upwardly open, preferably towards a lid. Other embodiments are possible however. As will be discussed below in greater detail, the receiving rack may, for example, be mounted rotatably, for example, about an axis, for example, a central axis. It is generally preferable if the receptacle is designed to hold the food and to enable cleaning fluid to run off from the receptacle after acting on the food. This can be achieved, for example, if the receptacle has one or preferably a plurality of openings which are dimensioned in such a way that the food is retained in the receptacle, but the cleaning fluid can run off. For example, the receptacle for this purpose may comprise one or more openings that have a diameter or equivalent diameter of no more than 20 mm, in particular of no more than 10 mm, for example, an equivalent diameter from 1 mm to 20 mm, in particular an equivalent diameter from 5 mm to 10 mm. In particular, the receptacle can be designed completely or partially as a grid or sieve, for example, as a grid-like receiving rack.

In particular, the receptacle may be movable, for example, if the cleaning apparatus comprises at least one actuator which is designed to position the receptacle in at least two positions. These positions may be arranged, for example, inside the cleaning chamber. The cleaning apparatus can be designed in particular to dip the receptacle in at least one first position at least partially into a cleaning bath, wherein the cleaning bath can be filled at least in part with the cleaning fluid. The cleaning bath may be arranged, for example, in a tank inside the cleaning chamber, for example, at the bottom of the cleaning chamber. Furthermore, the cleaning apparatus can be designed to arrange the receptacle in at least one second position, which is different from the first position, at least partially outside the cleaning bath, in particular at least partially outside the tank filled with the cleaning fluid. In particular, the cleaning apparatus can be designed to dip the receptacle into the cleaning bath and to lift it from the cleaning bath by means of at least one lowering/lifting movement, in particular periodically. For this purpose, the cleaning apparatus may comprise a lowering/lifting mechanism, for example.

The at least one plasma source can be designed, for example, to subject the food in at least one disinfection position, in particular in the second position, to the action of the reactive gas. For example, the controller can be designed in such a way that, in the disinfection step, the receptacle is or will be positioned in such a way that the food is arranged completely or partially outside the cleaning bath, for example, in the above-mentioned second position, wherein, in this disinfection step, the food is acted on by the reactive gas.

The receptacle can be mounted rotatably in particular. The cleaning apparatus may be designed in particular to rotate the receptacle in at least one position, in particular to rotate the receptacle with a speed of rotation of at least 10 revolutions per minute, preferably of at least 50 revolutions per minute, and particularly preferably of at least 100 revolutions per minute. This rotation can be used in one or more program steps. For example, at least one rotation can occur as the receptacle is dipped into the cleaning bath, for example, with a slow speed of rotation of, for example, less than 60 revolutions per minute, in particular of less than 30 revolutions per minute. During this rotation, the food may optionally also be acted on by cleaning fluid by means of at least one jet system, for example, by means of the optional wash jet system explained below in greater detail. Furthermore, at least one rotation may also occur alternatively or additionally in a position in which the receptacle is lifted completely or partially from the cleaning bath, for example, a rotation for the purpose of centrifuging cleaning fluid from the food and/or a rotation during which the food is acted on by cleaning fluid via at least one jet system, for example, via at least one fresh water rinse jet system explained below in greater detail. The rotation can also be driven, for example, by the cleaning fluid, for example, by spraying or blasting the cleaning fluid onto the receptacle or at least one drive element of the receptacle in such a way that the receptacle is rotated.

The cleaning apparatus may in particular comprise at least one jet system, which is designed to subject the food in the receptacle to the action of the cleaning fluid. For example, the jet system may comprise a first jet system which is arranged inside the above-mentioned cleaning bath, for example, at least one wash jet system, and may comprise at least one second jet system which is arranged outside the cleaning bath, for example, a fresh water rinse jet system.

The cleaning apparatus can carry out at least one self-cleaning step in particular, for example, by means of a corresponding embodiment of the controller. For example, once the food has been cleaned, at least one self-cleaning step can thus be carried out, in which the cleaning chamber is cleaned and/or disinfected, for example, once the food has been lifted from the cleaning chamber, by being subjected to the action of the cleaning fluid and/or by pumping off contaminated cleaning liquid and/or by being subjected to the action of the reactive gas.

Alternatively or additionally to the above-described embodiments, the cleaning apparatus may also comprise at least one transport system, wherein the transport system can be designed to transport the articles through the cleaning chamber or through part thereof. In particular, the cleaning apparatus can be designed in this embodiment as a pass-through dishwasher or may comprise at least one pass-through dishwasher. The transport system may, for example, comprise a belt, a link chain, a roller drive, or other types of known transport systems. The pass-through dishwasher can be designed, for example, as a flight-type dishwasher or as a rack conveyor dishwasher. The articles can be transported through the at least one cleaning chamber at the same speed, for example, or also at varying speed, wherein a transport speed, for example, can determine an intensity and/or duration with which the articles are acted on by the cleaning fluid.

The cleaning chamber may comprise a zone or in particular a plurality of zones. For example, these zones can be arranged in a common housing. These zones may in particular comprise at least one cleaning zone, in particular, a cleaning zone selected from a pre-rinse zone, a main cleaning zone, a pump final rinse zone, and a fresh water final rinse zone. Any combinations of the aforementioned cleaning zones are also conceivable. For example, at least one main cleaning zone can adjoin a pre-rinse zone in a direction of transport of the transport system, followed preferably by at least one final rinse zone, for example, at least one pump final rinse zone and then at least one fresh water final rinse zone. Furthermore, at least one drying zone may preferably be provided downstream of the at least one cleaning zone, in particular in the direction of transport, for example, at least one drying zone with at least one drying fan, via which the articles can be acted on, for example, by warm air for drying. Furthermore, at least one disinfection zone can be provided in the cleaning apparatus, for example, inside the cleaning chamber and/or in at least one separate disinfection chamber. The disinfection zone can be designed in particular in such a way that the articles are transported through the at least one disinfection zone by means of the transport system. The at least one disinfection zone may also be combined completely or partially with at least one of the aforementioned zones, for example, one or more of the cleaning zones and/or the at least one drying zone. In particular, the disinfection zone can be integrated completely or in part into the at least one drying zone. Once the articles have passed through the at least one disinfection zone, they are preferably no longer subjected to the action of the cleaning fluid, and therefore the at least one disinfection zone is preferably arranged at least largely at one end of the cleaning apparatus. The articles can generally be subjected at least once in the disinfection zone to the action of the at least one reactive gas.

As mentioned above, the articles are acted on at least in part by the at least one reactive gas by being brought completely or partially into contact with the reactive gas. Furthermore, the reactive gas can also be used to clean and/or to disinfect components of the cleaning apparatus. In particular, the cleaning apparatus can also be designed to bring at least part of the transport system into contact with the reactive gas, in particular at least a conveyor belt and/or at least a transport rack.

The cleaning apparatus may also be designed to generate inside the cleaning chamber a gas flow against a direction of transport of the transport system. For example, the gas flow can be generated by at least one fan and/or by at least one suction apparatus. For example, at least one fan can be provided in the at least one optional drying zone, said fan generating the gas flow completely or partially, for example, by directing said gas flow appropriately by means of corresponding guide elements, for example, deflector plates. Alternatively or additionally, at least one suction system can be provided, for example, in an inlet region of the cleaning apparatus. The cleaning apparatus, in particular, at an inlet region, may comprise at least one suction system, by means of which the gas flow against the direction of transport of the transport system can be generated completely or partially, where appropriate in cooperation with at least one fan. The cleaning apparatus, in particular, at an inlet region, may comprise at least one suction system with at least one preparation apparatus, wherein the preparation apparatus can be designed to remove the reactive gas at least in part from a suctioned-off air. The at least one preparation apparatus may, for example, comprise at least one filter and/or at least one catalyst, by means of which, for example, the reactive gas and/or parts of the reactive gas are removed from the suctioned-off air and/or are converted into other chemical compounds, for example, less reactive chemical compounds.

Generally, the cleaning apparatus can be designed, independently of the embodiment of the cleaning apparatus, to convey the reactive gas, after contact with the articles at least in part and optionally with at least part of the cleaning apparatus, through at least one preparation apparatus, in particular at least one filter and/or at least one catalyst. For example, harmful components can thus be removed at least in part from a waste gas of the waste disposal apparatus, for example, ozone, hydrogen peroxide, or other reactive components. For example, at least one activated carbon filter can be provided. Alternatively or additionally, at least one catalyst can be provided, for example, at least one platinum catalyst and/or at least one palladium catalyst.

The cleaning apparatus may generally comprise at least one pressure apparatus, wherein the pressure apparatus can be designed to generate at least one overpressure and/or at least one negative pressure in at least part of the cleaning apparatus, for example, the at least one cleaning chamber and/or the at least one disinfection chamber. For example, the pressure apparatus may comprise at least one suction apparatus and/or at least one fan. The pressure apparatus can be designed in particular to divert the reactive gas, after contact with at least part of the cleaning apparatus, into a drain system. This conveying process can be achieved, for example, by suction, displacement, washing out, or other types of removal of the reactive gas, for example, from the cleaning chamber and/or the disinfection chamber.

Further possible embodiments according to this disclosure concern the embodiment of the at least one plasma source. Generally, the plasma sources described in the above-mentioned prior art and/or also other plasma sources can be used, for example. As already discussed above, the plasma source may comprise in particular at least one first electrode and at least one second electrode. These electrodes can be arranged, for example, parallel to one another. For example, the electrodes can be designed as flat electrodes with an electrode surface area of at least one 100 mm$^2$, preferably at least 1,000 mm$^2$, in particular at least 10,000 mm$^2$, or even at least 100,000 mm$^2$, or at least 1,000,000 mm$^2$. If the plasma source comprises at least two electrodes, at least one of the electrodes may thus have a plurality of openings, for example, a plurality of perforations and/or meshes. In particular, at least one of the electrodes can be designed as a grid electrode, for example, in the form of a wire grid. In particular, metal materials are possible electrode materials. For example, at least one of the electrodes can be designed as sheet metal, for example, as a copper sheet electrode. The electrode with the plurality of openings can be designed, for example, as a mesh electrode formed from copper wire and/or stainless steel. At least one of the electrodes, for example, the electrode with the plurality of openings, can be earthed.

In particular, at least one dielectric can be arranged between the at least two electrodes. For example, this dielectric may comprise of plastic with insulating properties and/or a ceramic material. The dielectric can have a relative permittivity $\in r$ of 1-5, for example, of 1.1-4, for example, in particular of 1.5-2.5, and particularly preferably 2. For example, at least one polymer is a possible plastic material, for example, polytetrafluroethylene. Alternatively or additionally, other dielectric materials can also be used however. This described arrangement may also be described as an electrode assembly. An individual electrode assembly of this type can, together with an electric controller, generate the desired plasma. A plurality of electrode assemblies can also be arranged in the vicinity of one another in order to enrich a greater volume with plasma. At least two of these electrode assemblies can be arranged at a distance from one another from 0.5 mm-50 mm, for example, in particular from 1 mm-40 mm.

In particular, the plasma source can be designed in one or more of the following ways. The plasma source can be arranged in particular inside the cleaning chamber and can be designed to ignite the plasma inside the cleaning chamber. In this case, the gas in which the plasma is ignited is in particular directly connected to the atmosphere prevailing in the cleaning chamber or is at least partly identical thereto. Alternatively or additionally, the plasma source can also be arranged outside the cleaning chamber, however, and the cleaning apparatus can be designed to convey the reactive gas into at least part of the cleaning chamber, in particular by means of a fan, a suction apparatus or an overpressure apparatus. In this case, the external plasma source can be designed as a plasma donor, for example, and the reactive gas generated by the plasma source can be transferred into the cleaning chamber, for example, by being drawn in and/or blown in. For example, the external plasma donor can be arranged in the form of an add-on and/or a connection piece on the cleaning chamber, and the generated reactive gas can be introduced by this connection piece into the cleaning chamber. The connection piece and/or add-on may have a fan, for example, by means of which the reactive gas is introduced into the cleaning chamber.

The plasma source may also in particular comprise at least one electrical energy source. This electrical energy source can be designed to act on the electrodes by means of an A.C. voltage, which can include the possibility of embodiment as an A.C. voltage source and/or as an alternating current source. The electrical energy source can provide, for example, a voltage in a range from 1 kV-100 kV, for example, a peak-to-peak voltage, preferably a voltage from 5 kV-50 kV, particularly preferably from 10 kV-25 kV, and in particular 18 kV. If an A.C. voltage source is provided, this may have a frequency in the range from 100 Hz-100 kHz, for example, in particular in the range from 1 kHz-50 kHz, preferably from 5 kHz-20 kHz, and particularly preferably of approximately 12.5 kHz.

As described above, the gas in which the plasma is ignited may in particular comprise oxygen, for example, with a proportion from 1%-80%, in particular from 10%-30%, and particularly preferably of approximately 20%. In particular, the gas may be air. The air may preferably have a high moisture content, for example, a relative air humidity of more than 90%, preferably of more than 95%. Alternatively or additionally to the use of air, other gases may also be used however, and/or components that purposefully influence the ignition and/or composition of the plasma and/or the composition of the reactive gas can be added purposefully to the air.

The reactive gas, as mentioned above, may in particular comprise at least one plasma, in particular a cold plasma with a temperature of less than 100° C., preferably of less than 80° C., and particularly preferably of less than 60° C., or even less than 40° C. Corresponding temperatures may also apply for the reactive gas. The plasma may in particular have a ratio of charged particles to uncharged particles of 10-8-10-11, preferably of 10-9-10-10. The reactive gas may in particular have a pressure that does not deviate significantly from a normal pressure, for example, a pressure from 100 mbar-2,000 mbar, in particular a pressure from 500 mbar-1,500 mbar, preferably a pressure from 800 mbar-1,200 mbar, and particularly preferably normal pressure. The reactive gas may in particular comprise at least one compound that can be generated by the plasma, in particular a gaseous compound, wherein, besides gaseous compounds, liquid compounds can also be contained however in the reactive gas in principle. In particular, the reactive gas may comprise at least one compound which can be generated by the plasma, selected from the group consisting of: ozone, atomic oxygen, atomic nitrogen, and hydrogen peroxide.

As mentioned above, the plasma source may in particular also comprise at least one fan, wherein the fan is designed to convey the reactive gas into at least part of the cleaning apparatus, in particular into at least one cleaning chamber. For example, the fan can be designed in such a way that the reactive gas is guided directly onto the articles, for example, onto the surfaces to be cleaned of dinnerware, for example, plate surfaces, hollow spaces of glasses and/or cups, onto cutlery or the like, normally onto surfaces coming into contact with food. When cleaning other types of articles, the direction of the reactive gas can be selected differently. For example, the fan may be connected to a jet, such that a direction of the reactive gas can be purposefully selected. For example, the reactive gas can also be directed into an interior of pans, urine bottles or other vessels for receiving human excretions. When cleaning personal protective equipment, a direction of the reactive gas may likewise be purposefully selected, for example, into an inner region of masks, onto a mouthpiece, into an inner region of tubes or purposefully onto regions that may come into contact with sweat, saliva, other types of bodily fluids, or other types of contaminations.

In a further aspect of this disclosure, a method for cleaning articles is proposed. The articles can be selected in particular from the group consisting of: dinnerware; care utensils; food; and personal protective equipment. This method can be carried out in particular with use of a cleaning apparatus according to one or more of the above-described embodiments, and therefore reference can be made to the possible embodiments of the cleaning apparatus for possible embodiments of the method. Other embodiments are also possible however in principle. In the method, the articles are acted on in at least one cleaning chamber by at least one cleaning fluid. Furthermore, a plasma is ignited in at least one gas by means of at least one plasma source and generates at least one reactive gas. The reactive gas is brought into contact with the articles, at least in part. The reactive gas can be contacted with the articles in this way in particular inside the cleaning chamber and/or inside at least one disinfection chamber.

In a further aspect of this disclosure, a use of a reactive gas, generated from at least one gas by means of a plasma source, for cleaning articles in a cleaning apparatus is proposed, in particular for cleaning dinnerware, care utensils or personal protective equipment according to the above definitions.

The proposed cleaning apparatus, the proposed method and the proposed use have a large number of advantages compared to known apparatuses and methods. In particular, a cleaning and/or disinfection process can be carried out by means of the plasma source and by means of the reactive gas generated thereby, in particular with the at least one plasma, in a simple, reliable and comparatively cost-effective manner. The disinfection process can be carried out as a result of the fact that the cleaning chamber, for example, a treatment space and/or a washing chamber and/or a cleaning zone of a pass-through dishwasher, is filled with the reactive gas, in particular with the at least one plasma. For example, electrodes can be introduced into a wall and/or on a plurality of walls of the cleaning chamber and/or of the treatment space, for example, the disinfection chamber, and, for example, can convert the gas in the cleaning chamber or disinfection chamber, in particular normal air, at least partially into a plasma with use of electrical energy. This treatment step can take place in particular at normal pressure or under conditions deviating slightly therefrom, for example, overpressure or negative pressure. Alternatively or additionally, the plasma can also be generated in a separate plasma donor, which is connected, for example, by means of a pipeline, to the cleaning chamber and/or the disinfection chamber (both possibilities will also be referred to generally hereinafter as a "treatment space"). During a disinfection step, the plasma can be blown into the treatment space, for example, by means of a fan.

The disinfecting effect of plasmas, in particular cold plasmas, and/or the disinfecting effect of reactive gases generated by plasmas of this type is/are known from the above-described prior art, for example. In accordance with this disclosure, this disinfecting effect is transferred to the field of cleaning technology, for example, to dishwashing, the cleaning of food, in particular the washing of food of plant origin, the preparation of utensils from the field of patient care, and/or the preparation of personal protective equipment.

The reactive gas can be generated and/or initiated, in particular with the at least one plasma, in a relatively dry treatment space and/or in a treatment space that is filled with moist atmosphere, for example. It is also conceivable for additional treatment fluid and/or at least one gas component to be sprayed into the treatment space, for example, during the plasma generation and/or plasma initiation in order to influence the composition and/or the action of the reactive gas or of the plasma.

In a cleaning apparatus in which the articles to be treated remain stationary in a cleaning chamber during the entire treatment process, the treatment process can proceed, for example, as described above in the form of a sequence of program steps. Accordingly, the cleaning apparatus can be designed in particular as what is known as a programmable automatic machine. Alternatively or additionally, programs of this type can also be used, for example, with the above-described cleaning and disinfection units in many cases. In a cleaning program of this type with a plurality of program steps, at least one step may occur, for example, in which the articles are treated with the reactive gas, in particular containing the at least one plasma. This treatment step, which will also be referred to hereinafter as a plasma step, can occur, for example, as the last step before the end of a program. Alternatively or additionally, it is also conceivable however for the plasma step to occur already, for example, before a last final rinse. Any undesirable substances produced in the plasma can thus be washed out and therefore eliminated. Alternatively or additionally, it is also conceivable for the demand of final rinse aid, which, for example, exists in conventional programmable automatic machines and/or conventional cleaning and disinfection units, to be reduced by the use of the plasma, even down to zero depending on the circumstances. It is also conceivable for at least one plasma step to be added in even earlier phases of the treatment process, for example, in order to improve a cleaning action. At least one plasma step can be applied independently of whether or not the cleaning fluid in a tank is replaced during the course of a program. Embodiments of this disclosure and in particular the plasma treatment can thus be applied, for example, in domestic dishwashers, which, for example, are designed as water-change dishwashers and/or which, for example, have just one tank. Alternatively or additionally, these teachings can also be applied to multi-circuit dishwashers however, for example, dishwashers having a two-circuit system, as described above, which are typically provided for commercial use. Whereas, for domestic use, the cleaning fluid in the tank of the dishwasher is typically replaced, in a commercial dishwasher the cleaning fluid or at least part thereof normally remains in the machine during the program.

If the plasma step occurs as the last program step, the reactive gas, in particular the plasma, can thus be introduced into the treatment space by means of a fan, for example, and a drying effect on the articles can thus also be achieved, for example. Here, it is in particular advantageous that the drawn-in drying air can be disinfected automatically, for example, as it flows through the plasma donor. As mentioned above, a plasma source with a fan can be provided for this purpose, for example. The cleaning apparatus may comprise a suction connection piece, for example, which opens out into the plasma source and/or within which the plasma source is arranged. For example, the plasma can thus be generated at least in part in drawn-in fresh air, such that said fresh air is converted into the reactive gas and/or contains the reactive gas before said drawn-in fresh air is then introduced, for example, into the treatment space, in particular the cleaning chamber and/or the disinfection chamber. For example, the cleaning apparatus can be designed in such a way that the total amount of drawn-in fresh air and/or drying air is automatically disinfected by the plasma source.

With use of the plasma source in a pass-through dishwasher, for example, the pass-through dishwasher may have, for example, at least one special zone for treatment with the reactive gas, in particular for plasma treatment, and/or the at least one plasma source may be integrated into another zone of the pass-through dishwasher. For example, at least one disinfection zone, inside which the articles are subjected to the action of the reactive gas, can be provided before a final rinse zone, for example, before a last final rinse zone, through which the articles pass, after a final rinse zone and/or before or in a drying zone, which may or may not be provided, or downstream of a drying zone. Integration of one or more disinfection zones, in which the articles are subjected to the action of the reactive gas, further forwards in the treatment space is also conceivable, wherein a cleaning effect can be influenced positively by a subsequent application of cleaning fluid, for example.

As described above, the plasma can be ignited directly in the cleaning chamber and/or the disinfection chamber, for example. Alternatively or additionally, it is also conceivable however to design at least one plasma source, which can be designed as a plasma donor, in such a way that the reactive gas generated by said plasma source, in particular with the at least one plasma, flows through at least one optionally provided tank for the cleaning fluid and/or individual or all lines of an optional pipeline system, such that these are filled completely or partially with the reactive gas. A complete or partial system disinfection of the cleaning apparatus can thus be achieved. It is therefore particularly preferable if the plasma source is designed in such a way that the reactive gas is brought into contact with at least part of the fluid source. For example, the reactive gas can be brought into contact with one or more of the following components of the fluid source: at least one fluid tank, for example, a wash tank and/or an after rinse tank; at least one pipeline of a pipeline system of the fluid source, for example, a fresh water line and/or a wash line and/or an after rinse line; and at least one jet of the fluid source. In particular, the plasma source can be designed in such a way that the reactive gas is generated in at least one fluid tank of the cleaning apparatus. For example, the plasma can be ignited in a gas volume, for example, an air volume, above a liquid level in the fluid tank. For example, a plasma can be generated in a water tank of a dishwasher and/or of a cleaning and disinfection unit. The reactive gas can also come into contact with other component parts of the cleaning apparatus, for example. Besides the cleaning fluid, in particular an aqueous cleaning fluid, and also one or more lines which guide the cleaning fluid, any air ducts present and/or internal parts located therein, for example, such as at least one heat exchanger, can thus be brought into contact with the reactive gas where appropriate, such that these can also be disinfected, alternatively or additionally to the above-mentioned components.

A plasma treatment for bacteria reduction and/or disinfection can be used alone or in combination with chemical disinfection methods or also alone or in combination with thermal disinfection methods. Accordingly, the cleaning apparatus may optionally also comprise, in addition to the at least one plasma source, at least one metering apparatus for introducing at least one chemical disinfectant and/or at least one thermal disinfection apparatus, for example, by means of a steam source. It is particularly preferable however if the cleaning apparatus is designed without a chemical disinfection apparatus and/or without a thermal disinfection apparatus, and if disinfection occurs merely on account of the reactive gas.

As described above, the cleaning apparatus and the method can also be used for cleaning personal protective equipment, for example, for cleaning breathing masks. For example, a cleaning apparatus and a method can thus be produced, by means of which, for example, at least one breathing mask itself and/or airways of the breathing mask, for example, all airways, can be treated or acted on by the reactive gas, for example, at the end of a cleaning program. Other embodiments are also conceivable.

In contrast to conventional methods and apparatuses for disinfection of articles, the generation of a plasma and of a reactive gas therefrom requires a comparatively low use of energy. For example, embodiments taught herein differ considerably from cleaning apparatuses that are based exclusively on thermal disinfection, for example, exclusively on steam generation. For example, it is possible to dispense completely with thermal disinfection, or thermal disinfection can be considerably reduced compared to conventional apparatuses and methods, such that the total energy demand of the cleaning apparatus can be considerably reduced.

Furthermore, a period of action of the reactive gas on the components to be disinfected, in particular the articles, can be much shorter than a period of action of heat and/or chemical disinfectants, for example. Advantages with regard to the duration of the entire process are provided hereby. In particular, the throughput of articles in pass-through dishwashers can be considerably increased hereby. In programmable automatic machines, the total duration of the cleaning program can be significantly shortened compared to conventional programmable automatic machines, for example.

Advantages with regard to the temperatures prevailing during a disinfection process are also provided. For example, the articles on the whole can be exposed to considerably lower maximum temperatures during the entire treatment process. For example, the treatment in the cleaning apparatus or by means of the proposed method can be carried out in such a way that the articles are heated to temperatures of less than 95° C., preferably of less than 90° C., and particularly preferably of less than 85° C., or even less than 80° C. Even methods and apparatuses with which heating is carried out to no more than 70° C., no more than 60° C., or even no more than 50° C. can be provided. Accordingly, the articles can be quickly removed again and used again at the end of the treatment process, for example, once the cleaning program has finished and/or once passed through the pass-through dishwasher. A risk of injury to an operator caused by hot articles can be considerably reduced or even completely excluded. Furthermore, due to the possibility of providing lower temperatures, articles that are sensitive to higher temperatures can also be disinfected. For example, plastics, which have a comparatively low thermal resistance, for example, a low heat deflection temperature, for example, a heat deflection temperature HDT of less than 90° C., in particular of less than 85° C., can be disinfected.

A further advantage to be mentioned is the fact that it is possible to dispense with the use of dangerous substances or the fact that a use of dangerous and/or environmentally endangering substances can be at least largely avoided or reduced. For example, it is possible to dispense with the use of chemical disinfectants, or the quantity of chemical disinfectants of this type that are used can at least be reduced. Environmental compatibility and user friendliness are thus increased.

Furthermore, the properties of surfaces can also be changed due to the action of reactive gases and in particular of plasma. For example, the surface properties of the articles and/or of component parts of the cleaning apparatus can be changed with regard to their wettability. Effects of this type are known, for example, from the surface treatment of plastic parts, for example, before a coating process. For example, it is thus conceivable for a positive side effect with regard to a need and/or consumption of final rinse agent to be established due to the influence of the at least one reactive gas, in particular of the plasma.

Furthermore, an advantage of the action of the reactive gas, in particular of the plasma, to be mentioned is the fact that a disinfection effect is also attained in areas that in many cases cannot be reached by means of conventional disinfection methods. For example, the at least one reactive gas, in particular the at least one plasma can also infiltrate hollow spaces, for example, hollow spaces of drinks containers, for example, drinking glasses placed upside down, and/or hollow spaces of care utensils, such as pans, urine bottles, or similar care utensils. For example, a plasma can be formed in a wide area, for example, anywhere where an electric field prevails, and a plasma can therefore be formed over a wide area inside the reaction chamber. Alternatively or additionally, the reactive gas, after formation by means of the at least one plasma, can extend over a wide area of the cleaning chamber and/or of the disinfection chamber, for example, since the plasma is actively transferred into this area and/or, for example, by diffusion processes. An extensive disinfection effect can thus be achieved. Due to the at least one reactive gas, in particular the at least one plasma, storage tanks, liquid lines, air ducts, heat exchangers and other components of the cleaning apparatus can also be disinfected, for example, as described above. A greater operational reliability of the cleaning apparatus is thus achieved, and odor nuisances in the surrounding environment of the cleaning apparatus can also be prevented or at least reduced, for example. In particular, besides the articles, further component parts of the cleaning apparatus, for example, of the warewasher, including of the line system and/or internal parts of the cleaning apparatus, for example, can also be disinfected where appropriate.

The plasma source can be integrated in different ways in the cleaning apparatus, which may also be formed variably. For example, the plasma source can thus be connected to the at least one cleaning chamber and/or can be integrated into the at least one cleaning chamber. Alternatively or additionally, at least one disinfection chamber can be provided, which comprises the plasma source and/or which is connected to the plasma source. For example, an external drying device at the outlet of a dishwasher can be equipped with a plasma source. Alternatively or additionally, the plasma source may also be designed as a separate unit, in which, for example, a plasma source, in the form of a plasma shower, for example, can be integrated. A plasma source as an addition to a rack-pass-through dishwasher can also be produced, for example. Furthermore, the plasma source can also be designed in such a way that operating elements of the cleaning apparatus can be kept sterile by means of the reactive gas. For example, a plasma shower can be provided on a door handle and/or on an operator panel of a cleaning apparatus, for example, on an operator film, in particular on a cleaning and disinfection unit, for example, in order to keep said operator panel sterile and/or to disinfect said operator panel. On the whole, the concept according to this disclosure of designing a cleaning apparatus with at least one plasma source for generating at least one reactive gas can therefore be used in a very versatile manner and universally in the field of cleaning technology.

BRIEF DESCRIPTION OF THE DRAWINGS

Further details and features of the invention will emerge from the following description of exemplary embodiments. The invention is not limited to the exemplary embodiments. Like reference numerals in the individual figures denote here like and/or functionally like elements or elements corresponding to one another in terms of their functions.

DETAILED DESCRIPTION

Figure 1:
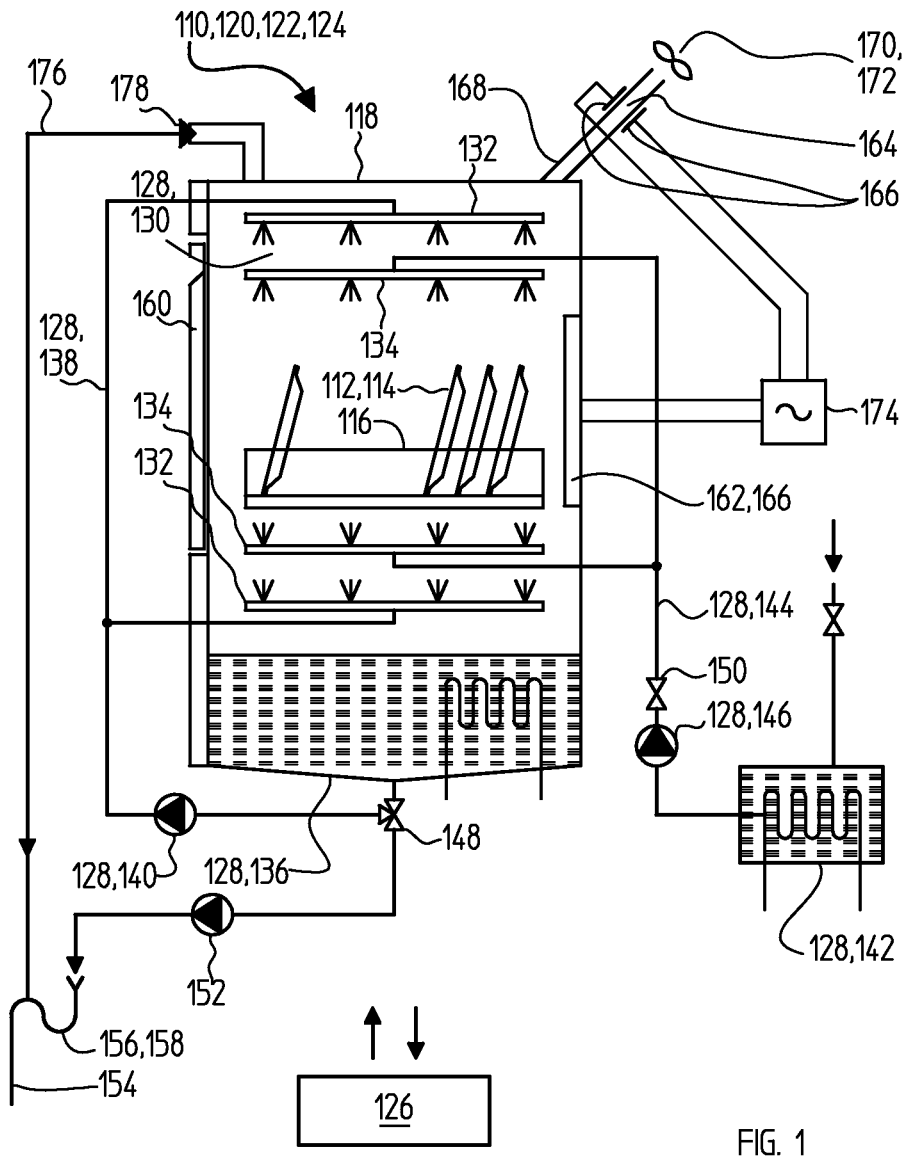
FIG. 1 shows an exemplary embodiment of a one-chamber warewasher, in particular, a one-chamber dishwasher, according to this disclosure.

A first exemplary embodiment of a cleaning apparatus 110 for cleaning articles 112 is illustrated in FIG. 1. The articles 112 are illustrated by way of example in the form of dinnerware 114. Alternatively or additionally, other types of articles 112 can also be considered, however, such as, as mentioned above, pieces of equipment belonging to personal protective equipment and/or other types of articles. The articles can be received, for example, in a receptacle 116 in the interior of a cleaning chamber 118, for example, in at least one rack, for example, in at least one dish rack. The cleaning apparatus 110 can therefore be designed in particular as a one-chamber warewasher 120 in the exemplary embodiment illustrated in FIG. 1, in particular, as a one-chamber dishwasher 122. The cleaning apparatus 110 can be designed in such a way that a cleaning program with optionally a plurality of cleaning program steps is carried out, and therefore the cleaning apparatus 110 can be designed, for example, as a programmable automatic machine 124. For this purpose, the cleaning apparatus 110 may comprise, for example, at least one controller 126, for example, with at least one data processing apparatus, optionally with at least one user interface (not illustrated), which, for example, can be programmed in order to control the cleaning program comprising the various cleaning program steps. This is illustrated symbolically in FIG. 1.

As mentioned above, the cleaning apparatus 110 comprises a cleaning chamber 118. A jet system 130 is provided in this cleaning chamber as a component of a fluid source 128. This jet system 130 may comprise one or more spray arms, for example, as illustrated in FIG. 1. For example, the jet system 130 may comprise jet arms arranged above the articles 112 and/or jet arms arranged below the articles 112. Here, different jet systems 130 can also be provided for the application of different types of cleaning fluid. A case in which a rinse jet system 132 with spray arms both above and below the articles 112 is provided, and an after rinse jet system 134, likewise with spray arms above and below the articles 112, is illustrated by way of example in FIG. 1. Other embodiments are also possible however in principle. The one-chamber warewasher 120 according to FIG. 1 can be designed as a multi-tank system, for example, as illustrated in FIG. 1, and, for example, may comprise at least one wash tank 136 at the bottom of the cleaning chamber 118, from which cleaning fluid is admitted to the rinse jet system 132 via a pipeline system 138 as a further component of the fluid source 128 and optionally via a pump 140. In addition, as illustrated in FIG. 1, at least one after rinse tank 142 can be formed separately from the wash tank 136, which is designed here by way of example as a boiler.

Other embodiments are also possible however in principle, for example, embodiments in which an after rinse liquid is heated via at least one tankless water heater. Similarly to the wash tank 136, the after rinse tank 142 may likewise be a component of the fluid source 128 and may have a pipeline system 144 and optionally a pump 146, via which cleaning fluid in the form of after rinse liquid, for example, fresh water, is admitted to the after rinse jet system 134, optionally with addition of additives. Furthermore, the fluid source 128 may have one or more valves, wherein valves 148 and 150 are illustrated by way of example in FIG. 1. The valve 148 can be provided at the outlet of the wash tank 136, for example, and can be designed as a 3-way valve, for example. This can be connected, for example, optionally via a further pump 152, to at least one drain 154, preferably a drain 154 with an odor trap 156, for example, a siphon bend 158. The controller 126 can be designed, for example, to control one or more of the pumps 140, 146, 152 and/or one or more of the valves 148, 150.

The articles 112 can be introduced, for example, through at least one opening 160 into an interior of the cleaning chamber 118. This at least one opening 160 can be designed in a closable manner, for example, in particular by a hatch, as shown in FIG. 1. Other closure mechanisms can also be used alternatively or additionally, however, for example, hinged doors, sliders, hinged parts of a hood, displaceable hoods, or other types of closable openings.

The cleaning apparatus 110 according to the exemplary embodiment in FIG. 1 further comprises at least one plasma source 162, 164. In the illustrated exemplary embodiment, two possibilities are provided, which can be used individually or in combination. For example, a first plasma source 162 may be provided, comprising electrodes 166, which are merely indicated in FIG. 1 and can be arranged inside the cleaning chamber 118 and/or inside a wall of the cleaning chamber 118. Reference can be made to the above prior art, for example, with regard to the embodiment of these electrodes. This plasma source 162 can be designed, for example, to ignite a plasma in a gas, for example, air, in particular with a high moisture proportion, located in the interior of the cleaning apparatus 118, whereby a reactive gas is in turn generated and preferably comprises said plasma.

Alternatively or additionally, at least one plasma source 164 arranged outside the cleaning chamber 118 can be provided and can be designed as a plasma donor, for example. In the exemplary embodiment illustrated in FIG. 1, the plasma source 164 can be designed in turn with electrodes 166, for example. This plasma source 164, which can be designed as a plasma donor, can be arranged in a supply air connection piece 168, for example, which opens out into the cleaning chamber 118. This supply air connection piece 168 can be equipped with and/or connected to a fan 170, which, for example, can be designed as a component of a pressure apparatus 172, in particular for generating an overpressure, or can be designed simply for feeding fresh air into the cleaning chamber 118. For example, by means of the plasma source 164, a plasma can be ignited in a gas located in the supply air connection piece 168 and can be used to generate a reactive gas, which can then in turn be transferred by the fan 170 into the interior of the cleaning chamber 118, where it can be applied purposefully to the articles 112, for example. The plasma sources 162, 164 can each be connected individually or jointly to at least one electrical energy source 174, for example, which is merely indicated in FIG. 1 and which, for example, may comprise an A.C. voltage source and/or an alternating current source. The plasma sources 162, 164 and/or the electrical energy sources 174 can likewise be controlled and/or activated by the controller 126, such that the generation of the plasma can likewise be controlled by the controller 126, for example. The controller can be designed, for example, to control at least one cleaning program in the cleaning apparatus, wherein the articles 112 are acted on by the cleaning fluid in at least one cleaning program step of the cleaning program, and wherein the articles 112 are acted on by the reactive gas in at least one disinfection step of the cleaning program, preferably once the cleaning program step has been carried out, for example, during a drying step. Alternatively or additionally, the disinfection step may also be carried out before a rinse step or final rinse step, for example, as mentioned above, and therefore contaminations and/or residues of the reactive gas adhering to the articles 112 can be removed by the after rinse fluid in the after rinse step or final rinse step, for example. Various other embodiments are possible. To initiate the disinfection step, the controller 126 can control the electrical energy sources 174 accordingly and/or can control the fan 170 accordingly, for example.

Furthermore, the cleaning apparatus 110 can be designed, as likewise shown by way of example in FIG. 1, to convey the reactive gas from the cleaning chamber 118 into the drain 154. This can be achieved, for example, by means of a positive displacement from the cleaning chamber 118. For this purpose, an exhaust air duct 176 can be provided, for example, which connects the cleaning chamber 118 to the drain 154, preferably after the odor trap 156, such that the odor trap 156 is arranged between a branch of the exhaust air duct 176 and a connection to the cleaning chamber 118. The exhaust air duct 176 may comprise one or more valves, for example, in particular, as indicated in FIG. 1, at least one check valve 178, for example, in order to prevent gases and/or liquids from the drain 154 from being able to travel back into the cleaning chamber 118. The cleaning apparatus 110 can be designed, for example, in such a way that reactive gas from the cleaning chamber 118 can be displaced via the exhaust air duct 176 into the drain 154, for example, by introducing pressurized supply air and/or steam, for example, by means of the fan 170. This displacement can in turn be controlled, for example, by the controller 126, for example, after completion of a disinfection step of a cleaning program.

Figure 2:
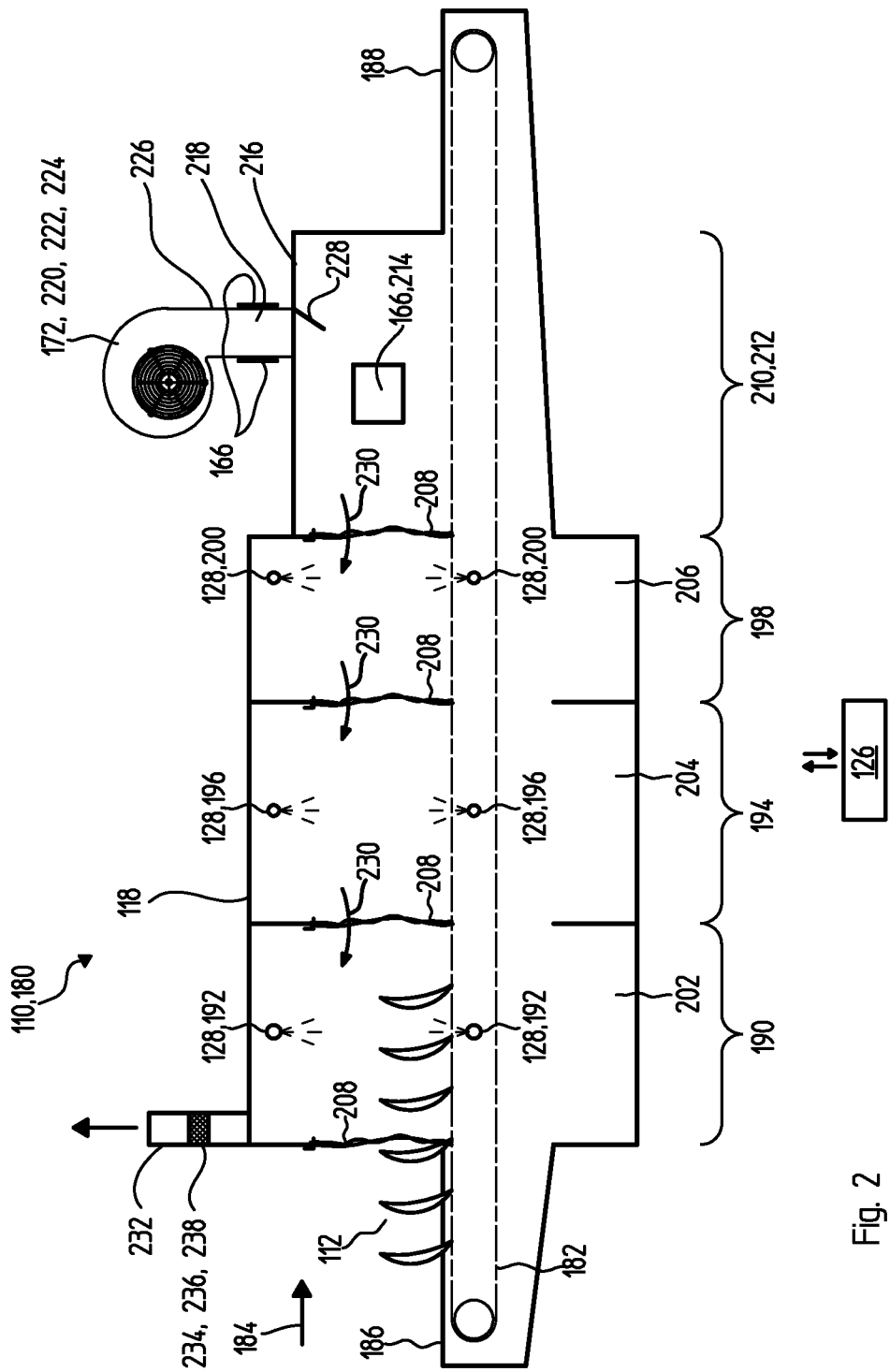
FIG. 2 shows an exemplary embodiment of a pass-through dishwasher according to this disclosure.

A further exemplary embodiment of a cleaning apparatus 110 according to this disclosure is illustrated in FIG. 2. In this exemplary embodiment, the cleaning apparatus 110 is designed as a pass-through dishwasher 180. The pass-through dishwasher again comprises a cleaning chamber 118, which in this exemplary embodiment is designed as a tunnel by way of example. For example, a transport system 182 can be provided, in particular a conveyor belt, by means of which articles 112 are conveyed in a transport direction 184 from an inlet 186 to an outlet 188. For possible details of the embodiment of the pass-through dishwasher 180, reference can be made to the above-described prior art, for example, to DE 10 2006 039 434 A1. Other embodiments are also possible however in principle. The pass-through dishwasher 180 can be designed, for example, as a flight-type dishwasher or rack conveyor dishwasher, for example.

Also in the exemplary embodiment shown in FIG. 2, the cleaning apparatus 110 again comprises a fluid source 128, which in this exemplary embodiment comprises a plurality of jet systems. The cleaning chamber 118 is thus preferably divided into a plurality of zones, specifically a pre-rinse zone 190 with a pre-rinse jet system 192, at least one main cleaning zone 194 with at least one main cleaning jet system 196, and at least one after rinse zone 198, which can also be embodied and/or referred to as a final rinse zone, with at least one after rinse jet system 200, for example, at least one pump final rinse jet system and/or at least one fresh water final rinse jet system. The jet systems 192, 196 and 200 can be supplied with cleaning fluid from corresponding tanks 202 to 206 via pumps (not illustrated in FIG. 2). The cleaning zones 190, 194, 198 can be separated from one another and/or can each be separated outwardly by curtains 208. At least one drying zone 210, for example, can adjoin the cleaning zones 190, 194, 198 and in this exemplary embodiment may optionally also be embodied at the same time as the disinfection zone 212. Alternatively or additionally, a disinfection process can also occur however in a separate disinfection zone, and/or a disinfection zone 212 can be combined with one or more of the cleaning zones 190, 194 or 198.

The cleaning apparatus 110 again comprises at least one plasma source 214, for example, again with at least two electrodes 166, as indicated in FIG. 2. The electrodes 166 can again be arranged, for example, similarly to the embodiment according to FIG. 1, in a wall of the cleaning chamber 118 and/or in a disinfection chamber 216, which surrounds the disinfection zone 212 and can be formed separately from the cleaning chamber 118 and/or can also be completely or partially identical thereto. Alternatively or additionally, as likewise indicated in FIG. 2, at least one plasma source 218, again with electrodes 166, for example, can again be arranged outside the cleaning chamber 118 and/or outside the disinfection chamber 216, for example, as a separate plasma donor. For example, at least one fan 220 may again be provided, for example, as a component of a pressure apparatus 172 and/or as a component of a drying apparatus 222 and/or as a separate apparatus. By way of example in FIG. 2, without limitation of further possible embodiments, the fan 220 is embodied as a drying fan 224, which can be connected via a supply air connection piece 226 to the drying zone 210 in order to apply air, preferably heated air, to the articles 112 in said drying zone 210. The plasma sources 214, 218 can again be designed to generate a plasma in a gas, whereby a reactive gas, preferably containing the plasma or part thereof, is again generated.

With the plasma source 214, the plasma can be generated directly in the disinfection chamber 216, for example, and/or, with arrangement in one or more of the cleaning chambers 190, 194, 198, in said cleaning chamber(s). With the plasma source 218, the plasma can be generated in the supply air connection piece 226, for example, and can then be applied to the articles 112 by means of a supply airflow generated by the fan 220, for example. The supply airflow and, with this, the reactive gas that is generated by the plasma source 218 can be influenced in terms of their direction, for example, by means of one or more flow conduction elements 228, for example, in order to give the supply airflow a direction against the transport direction 184. An airflow 230, which is directed against the transport direction 184, can thus be generated inside the cleaning apparatus 110, for example. With this airflow, the reactive gas can also be transported against the transport direction 184, for example.

The cleaning apparatus 110, as likewise indicated in FIG. 2, may further comprise at least one suction system 232, for example, in the region of the inlet 186. This suction system 232 can be connected, for example, to an exhaust air connection piece (not illustrated in FIG. 2), for example, in a roof region of a building in which the cleaning apparatus 110 according to FIG. 2 is arranged. In particular, at least one preparation apparatus 234, for example, at least one filter 236 and/or at least one catalyst 238, can be provided within the suction system 232, which, for example, may in turn comprise a fan. For example, the reactive gas and/or constituents thereof can thus be removed from an exhaust airflow and/or converted into less critical components. A preparation apparatus 234 of this type can optionally also be provided in other embodiments of the cleaning apparatus 110, for example, in the cleaning apparatus 110 according to FIG. 1, for example, in the exhaust air duct 176.

The cleaning apparatus 110 according to the embodiment in FIG. 2 may optionally again comprise at least one controller 126. This controller 126 can control the transport system 182 and/or the fluid source 128 and/or the plasma sources 214, 218, for example. The plasma sources 214, 218 may again be connected to one or more electrical energy sources 174, which is not illustrated in FIG. 2, for example, similarly to the embodiment according to FIG. 1. The embodiment of the optional electrodes 166 can be implemented, for example, again according to the above-described prior art.

Figure 3:
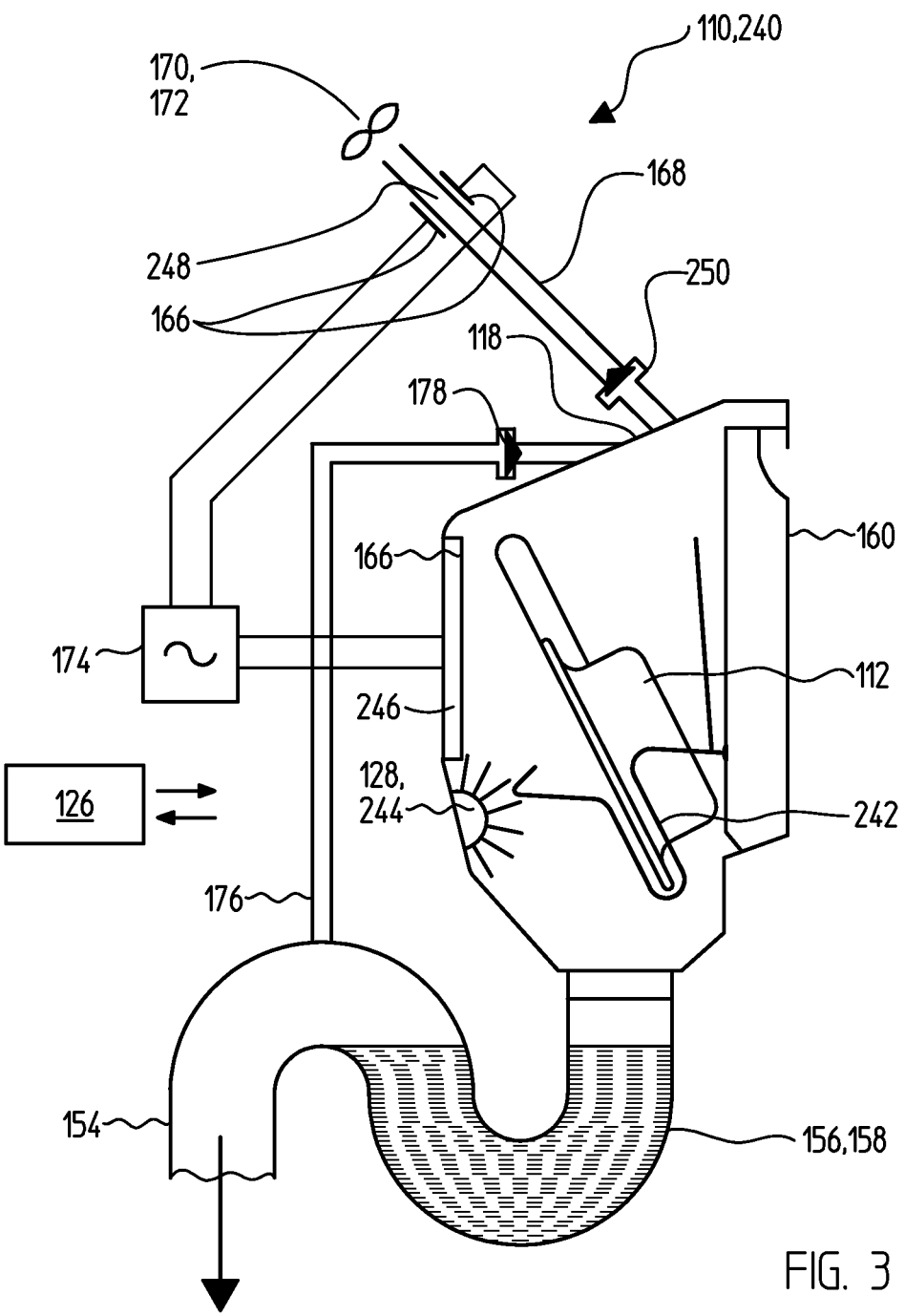
FIG. 3 shows an exemplary embodiment of a cleaning and disinfection unit according to this disclosure.

A further exemplary embodiment of a cleaning apparatus 110 according to this disclosure is illustrated in FIG. 3 in a sectional illustration similar to FIGS. 1 and 2. The cleaning apparatus 110 is formed in this exemplary embodiment as a cleaning and disinfection unit 240 and, for example, is formed for cleaning articles 112 in the form of pans, urine bottles, or the like. The cleaning apparatus 110 again comprises a cleaning chamber 118, in the interior of which the articles 112 can be received. For example, the cleaning chamber 118 may again, similarly to the embodiment according to FIG. 1, comprise a closable opening 160, for example, again with a hatch. A holder 242 as a receptacle for the articles 112 can be connected to the hatch, for example, such that, when the cleaning chamber 118 is closed, the articles 112 are emptied, such that solid and/or liquid waste can be emptied from the inside of the articles 112. For this purpose, the cleaning apparatus 110 may comprise at least one drain 154, which, for example, is formed with a diameter of such a size that the excretions and in particular relatively large quantities of liquid can be received without difficulty. The drain 154 can be formed again with an odor trap 156, for example, in particular a siphon bend 158.

The cleaning apparatus 110 according to the exemplary embodiment in FIG. 3 again comprises at least one fluid source 128, in particular in the form of at least one jet system 244. The articles 112 can be acted on via said jet system 244, for example, by cleaning fluid in the form of liquid and/or steam. Further components of the fluid source 128, for example, one or more liquid tanks and/or one or more pumps and/or one or more steam generators, are not illustrated in FIG. 3 for simplification. For further possible embodiments of the cleaning apparatus 110, reference can be made, for example, to the above-described prior art, in particular to DE 103 48 344 B4 and/or EP 1 824 373 B1.

The cleaning apparatus 110 may again have one or more plasma sources 246, 248, for example, again each with electrodes 166, for example, according to the above-described embodiment. The plasma sources 246, 248 can also again be connected to one or more electrical energy sources 174. Again, the possibilities already explained with reference to the example in FIG. 1 are illustrated and can be implemented individually or also in combination. The at least one plasma source 246 according to FIG. 3 is thus optionally arranged completely or partially in the interior of the cleaning chamber 118, such that a plasma can be ignited directly in the interior of the cleaning chamber 1118. Alternatively or additionally, the at least one plasma source 248 is provided and can generate a plasma in a supply air connection piece 168, which can optionally be equipped with and/or connected to at least one fan 170 as a component of a pressure apparatus 172. The plasma source 248 thus acts as a plasma donor and generates the plasma, for example, in a gas within the supply air connection piece 168, which can then be introduced, for example by means of the pressure apparatus 172, in particular the fan 170, into the cleaning chamber 118, in particular at overpressure. The supply air connection piece 168 may, for example, also again be provided with at least one valve 250. This embodiment can also be implemented in the exemplary embodiment according to FIG. 1 or in other exemplary embodiments of the cleaning apparatus 110.

The cleaning apparatus 110 may again comprise at least one controller 126, which, for example, can be designed to control the fluid source 128 and/or the plasma sources 246, 248. Furthermore, the fan 170 can also be controlled by the controller 126, for example. The controller 126 can again be designed, similarly, for example, to the embodiment according to FIG. 1, to carry out at least one cleaning program, for example, comprising at least one cleaning program step, in which the articles 112 are acted on by cleaning fluid, and at least one disinfection step, in which the articles 112 are acted on by the plasma or the reactive gas generated by one or more of the plasma sources 246, 248.

Similarly to the embodiment according to FIG. 1, the cleaning apparatus 110 in the exemplary embodiment according to FIG. 3 may also again comprise at least one exhaust air duct 176, optionally again with at least one valve 178, for example, at least one check valve. The exhaust air duct 176 can, for example, transfer reactive gas and/or other gas constituents and/or steam from the cleaning chamber 118 into the drain 154. Again, a branch of the exhaust air duct 176 is preferably arranged on the other side of the odor trap 156, for example, on the other side of the siphon bend 158, such that the odor trap 156 is arranged between said branch and the cleaning chamber 118. For example, due to the pressure apparatus 172, the reactive gas and/or constituents thereof can therefore be displaced via the exhaust air duct 176 into the drain 154. Alternatively or additionally, similarly to the exemplary embodiment according to FIG. 1, the reactive gas can also again be washed out and/or removed in another manner. For example, in the exemplary embodiment according to FIG. 3, as in the exemplary embodiment according to FIG. 1, at least one ventilation system and/or suction system can be provided, optionally again with at least one preparation apparatus 234, similarly to the exemplary embodiment according to FIG. 2.

Figure 4A:
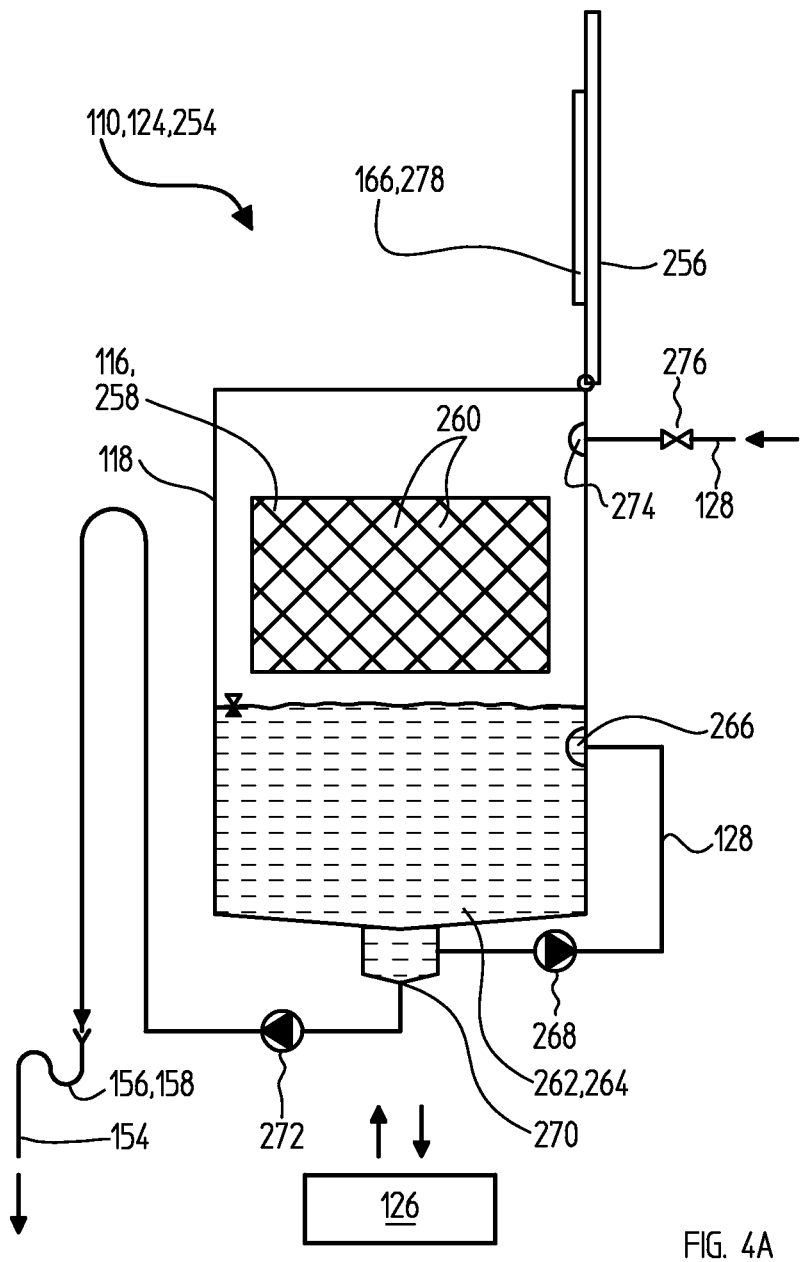
FIGS. 4A to 4C show various positions of an exemplary embodiment of a cleaning apparatus designed for cleaning foods.
Figure 4B:
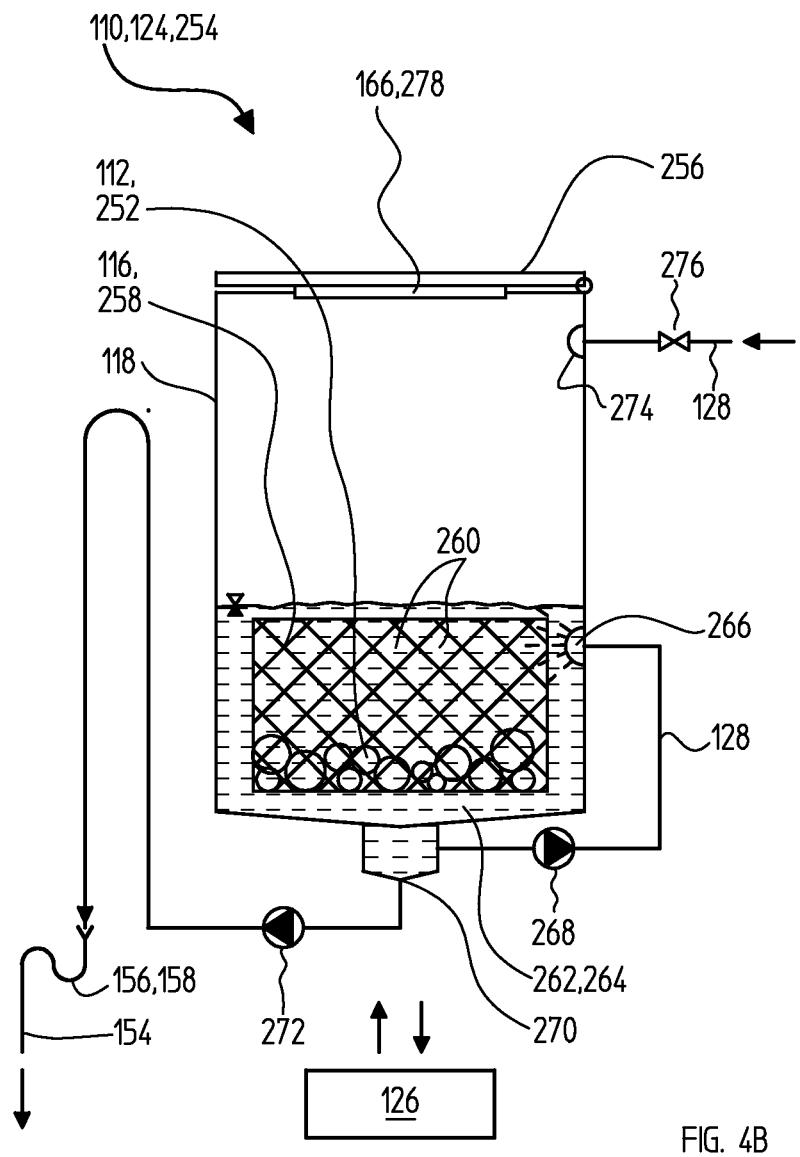
Figure 4C:
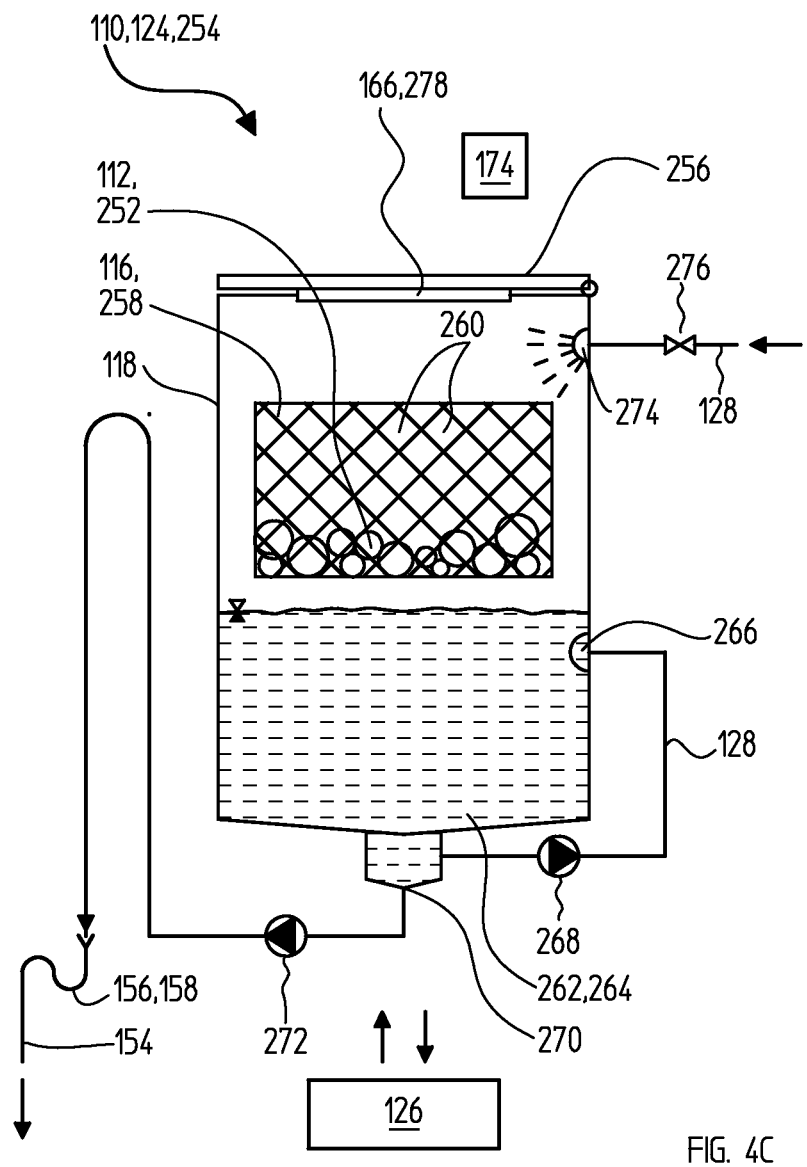

An exemplary embodiment of a cleaning apparatus 110 which is designed to clean articles 112 in the form of foods 252 is illustrated in FIGS. 4A to 4C. For example, as mentioned above, the foods can be vegetables, salad, fruit, berries, tubers, or similar foods, in particular foods of plant origin. The cleaning apparatus 110 can therefore be embodied in particular as a vegetable washing machine 254.

The cleaning apparatus 110 in the exemplary embodiment illustrated again comprises a cleaning chamber 118, which in this exemplary embodiment is loaded from above by way of example. The cleaning apparatus 110 is therefore formed, for example, as a toploader and, for this purpose, comprises a lid 256, for example, which can be opened in order to load the cleaning chamber 118 with the articles 112.

The cleaning apparatus 110 again comprises a receptacle 116 for the articles 112. In this exemplary embodiment, the receptacle 116 may be a basket 258 in particular, for example, a basket 258 produced from at least one metal material and/or from at least one plastic material. The receptacle 116 can be produced completely or partially from a plastic material and/or from a metal material. The receptacle 116 is designed to retain the food 252 during a cleaning procedure, but simultaneously to enable cleaning fluid to run off and preferably also to infiltrate, for example, by means of a plurality of openings 260 which are dimensioned accordingly. The basket 258 can be upwardly open and downwardly closed in FIGS. 4A to 4C, for example. The basket can be round, for example, for example, through a vertical axis in the drawing plane in FIGS. 4A to 4C.

The cleaning apparatus 110 in the exemplary embodiment illustrated in FIGS. 4A to 4C may again be formed as a one-chamber machine, for example. Embodiments with more than one cleaning chamber 118 are also possible however in principle.

The cleaning apparatus 110 may comprise, for example, in particular inside the cleaning chamber 118, at least one cleaning bath 262, into which the food 252 can be dipped by means of the receptacle 116. In the exemplary embodiment illustrated, the cleaning bath 262 is formed at the bottom of the cleaning chamber 118 in the form of a wash tank 264. The cleaning apparatus 110 can be formed in particular in such a way that the food 252 is arranged in at least one first position inside the cleaning bath 262 and in at least one further position outside the cleaning bath 262. This is illustrated in FIGS. 4A to 4C. FIG. 4A thus shows a position that, here, will also be referred to hereinafter as a "second position" (without specifying an order by means of this naming), in which the lid 256 is open and the cleaning apparatus 110 can be loaded with the food 252. The position illustrated in FIG. 4A is therefore a position for loading and/or unloading the articles 112 into/from the cleaning apparatus 110. By contrast, FIG. 4B shows a position that is also referred to here and hereinafter as a "first position", in which the receptacle 116 is loaded with the food 252 and in which the food 252 dips into the cleaning bath 262. For example, this dipping may be complete. In this dipped position according to FIG. 4B, the receptacle 116 may also be movably mounted, for example rotatably mounted. For example, the receptacle 116 may thus be rotatably mounted about an axis (not illustrated in FIG. 4B) running vertically in the drawing plane, for example, about an axis perpendicular to the liquid surface of the cleaning fluid in the cleaning bath 262. This rotation may be driven, for example, by the cleaning apparatus 110 by means of at least one motor and/or fluidically. For example, at least one wash jet system 266 may thus be provided in the cleaning bath 262 and can be acted on, for example, by cleaning fluid from the washing tank 264 via at least one wash pump 268. This wash jet system 266 can blast a jet with a tangential component onto and/or into the receptacle 116, for example, such that the food 252 in the receptacle 116 is acted on by cleaning fluid and/or an intensified flow and/or jet of the cleaning fluid. At the same time, this jet and/or flow of the cleaning fluid may optionally drive a rotation of the receptacle 116. For example, the receptacle 116 may have wings for this purpose, which are driven by the cleaning fluid. The food 252, for example, can thus be dipped into the bath of the cleaning fluid, for example, into a water bath, and rotated slowly, wherein cleaning fluid flows over and/or flows through said food. A lowering/lifting device may optionally be provided, for example, as a component of the above-mentioned actuator mechanism, and regularly or irregularly, for example periodically, lifts and lowers the receptacle 116 from and into the cleaning bath 262, wherein adhering contaminations can be detached and removed. The fact that the cleaning fluid flows over the food 252 in this way, combined with the optional upwards and downwards movement, can result in intensive cleaning with simultaneous protection of the sensitive food 252. The wash tank 264 can be emptied, for example, via an outlet 270 and an optional emptying pump 272, for example, into a drain 154, which may optionally be formed again with an odor trap 156 in the form of a siphon bend 158.

Whereas the position shown in FIG. 4B, in which the receptacle 116 is located in the first position, can be referred to as a cleaning position, a position that could also be referred to as a final rinse position or generally as a post-treatment position is shown lastly in FIG. 4C. In this position, the receptacle 116 is located in a second position, in which the food 252 is no longer dipped into the cleaning bath 262. For example, for this purpose, the receptacle 116 can be lifted from the cleaning bath 262, for example, again by means of an actuator mechanism (not illustrated). The position of the receptacle 116 in FIG. 4C may therefore correspond to the position of the receptacle 116 in FIG. 4A. Here, as shown in FIG. 4C, the lid 256 can be closed.

In this position, the food 252 can be subjected in succession or simultaneously to one or more treatment processes, for example, one or more post-treatment processes. An optional possibility, which is illustrated in FIG. 4C, is a treatment via at least one rinse jet system 274, which, for example, can be arranged in a chamber wall of the cleaning chamber 118, similarly to the wash jet system 266. Again, the food 252 can be acted on by a cleaning fluid, which preferably has a tangential component, by means of said rinse jet system 274, for example. The receptacle 116 can thus also be rotated, for example, in the second position of the receptacle 116 illustrated in FIG. 4C, said rotation being driven, for example, by a motor and/or by the cleaning fluid by means of the rinse jet system 274. The cleaning fluid of the rinse jet system 274 may be fresh water, for example, of which the inflow can be controlled by a valve 276, for example, a fresh water valve. For example, the cleaning fluid may comprise a rinsing fluid, in particular fresh water, which can again preferably infiltrate the receptacle 116 through the openings 260 in order to subject the food 252 to an after rinse process. For example, a fresh water after rinse may thus be provided, preferably by means of clear mains water.

A centrifugation procedure, in which the receptacle 116 is rotated and adhering cleaning fluid is removed by means of centrifugal forces, for example, may optionally adjoin said after rinse process in the second position illustrated in FIG. 4C. This centrifugation procedure can again be driven by motor, for example, or also by a fluid drive, for example, by means of the rinse jet system 274.

At least one disinfection step also adjoins before, during, or after one or more of the previously mentioned steps, which, with the exception of the centrifugation step, can be referred to as cleaning program steps. For this purpose, the cleaning apparatus 110 again comprises at least one plasma source 278. In the exemplary embodiments shown in FIGS. 4A to 4C, said plasma source 278 is received by way of example on an inner face of the lid 256 pointing towards the cleaning chamber 118. Alternatively or additionally, other embodiments are also possible however, for example, by attachment to one or more inner walls of the cleaning chamber 118 and/or in the form of one or more plasma donors, which can be arranged outside the cleaning chamber. With regard to these possibilities, reference can be made to the above description of the other exemplary embodiments. The possibilities presented there for the embodiment of the plasma source can also be used in principle, individually or in combination, within the scope of the vegetable washing machine 254 illustrated in FIGS. 4A to 4C. For example, as shown in FIG. 4C, the plasma source 278 may again comprise one or more electrodes 166, for example, on the inner face of the lid 256. Alternatively or additionally, one or more electrodes 166 may also be arranged, for example, in a supply air connection piece (not illustrated in FIGS. 4A to 4C). The plasma source 278 may again optionally comprise at least one electrical energy source 174, as illustrated optionally in FIG. 4C. The disinfection step by means of the plasma source 278 can occur in the second position of the receptacle 116 shown in FIG. 4C and/or in a separate disinfection position. Various embodiments are conceivable.

The cleaning apparatus 110 may again comprise one or more controllers 126, as indicated in FIGS. 4A to 4C, and in particular can be formed as a programmable automatic machine 124. Other embodiments are also possible however in principle. For example, a cleaning program in the cleaning apparatus 110 can be controlled by means of the controller 126 and, for example, initially allows the receptacle 116 to be loaded with the food 252, for example, in the position shown in FIG. 4A. At least one cleaning program step may then be carried out. This at least one cleaning program step may, for example, comprise at least one washing step, for example, according to the above description of FIG. 4B. At least one cleaning program step in the form of at least one rinsing step may optionally adjoin said at least one washing step, for example, in the form of at least one fresh water after rinse, for example, according to the above description of FIG. 4C. At least one drying step, for example, the above-mentioned at least one optional centrifugation step, may optionally adjoin said at least one optional after rinse step. This may likewise be carried out, for example, in accordance with the above description of FIG. 4C. Furthermore, the controller 126 can be designed to carry out at least one disinfection step before, during or after the at least one cleaning program step and/or between a plurality of cleaning program steps. In particular, this can occur in the position illustrated in FIG. 4C. In this at least one disinfection step, the food 252 is acted on by the reactive gas generated by the at least one plasma source 278, for example, as a result of the fact that said reactive gas rinses over or rinses through the food 252. For this purpose, the reactive gas can infiltrate the basket 258 from above and/or through the openings 260, for example, and can rinse over and/or can rinse through the food 252. Gentle disinfection of the food 252 can thus be achieved, preferably without use of chemical disinfectants and/or heat.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMERAL DESIGNATIONS

| | |
|---|---|
| 110 | cleaning apparatus |
| 112 | articles |
| 114 | dinnerware |
| 116 | receptacle |
| 118 | cleaning chamber |
| 120 | one-chamber warewasher |
| 122 | one-chamber dishwasher |
| 124 | programmable automatic machine |
| 126 | controller |
| 128 | fluid source |
| 130 | jet system |
| 132 | rinse jet system |
| 134 | after rinse jet system |
| 136 | wash tank |
| 138 | pipeline system |
| 140 | pump |
| 142 | after rinse tank |
| 144 | pipeline system |
| 146 | pump |
| 148 | valve |
| 150 | valve |
| 152 | pump |
| 154 | drain |
| 156 | odor trap |
| 158 | siphon bend |
| 160 | opening |
| 162 | plasma source |
| 164 | plasma source |
| 166 | electrode |
| 168 | supply air connection piece |
| 170 | fan |
| 172 | pressure apparatus |
| 174 | electrical energy source |
| 176 | exhaust air duct |
| 178 | check valve |
| 180 | pass-through dishwasher |
| 182 | transport system |
| 184 | transport direction |
| 186 | inlet |
| 188 | outlet |
| 190 | pre-rinse zone |
| 192 | pre-rinse jet system |
| 194 | main cleaning zone |
| 196 | main cleaning jet system |
| 198 | after rinse zone |
| 200 | after rinse jet system |
| 202 | tank |
| 204 | tank |
| 206 | tank |
| 208 | curtain |
| 210 | drying zone |
| 212 | disinfection zone |
| 214 | plasma source |
| 216 | disinfection chamber |
| 218 | plasma source |
| 220 | fan |
| 222 | drying device |
| 224 | drying fan |
| 226 | supply air connection piece |
| 228 | flow-conducting elements |
| 230 | airflow |
| 232 | suction system |
| 234 | preparation apparatus |
| 236 | filter |
| 238 | catalyst |
| 240 | cleaning and disinfection unit |
| 242 | holder |
| 244 | jet system |
| 246 | plasma source |
| 248 | plasma source |
| 250 | valve |
| 252 | food |
| 254 | vegetable washing machine |
| 256 | lid |
| 258 | basket |
| 260 | openings |
| 262 | cleaning bath |
| 264 | wash tank |
| 266 | wash jet system |
| 268 | wash pump |
| 270 | outlet |
| 272 | emptying pump |
| 274 | rinse jet system |
| 276 | valve |
| 278 | plasma source |

What is claimed is:

1. A cleaning apparatus for cleaning articles, comprising:
exactly one sealable cleaning chamber that can be opened and closed to insert and remove the articles, the cleaning chamber comprising a fluid source for subjecting the articles to the action of a cleaning fluid;

a plasma source configured to ignite a plasma in a gas and to generate a reactive gas, wherein the cleaning apparatus is configured to bring the reactive gas into contact with the articles; and a cleaning and disinfection unit for cleaning care utensils, wherein the care utensils are suitable for receiving one or both of liquid and solid human excretions of at least 100 ml, the cleaning and disinfection unit comprising a drain for the disposal of excretions contained in the care utensils, the drain being formed with an odor trap;

wherein, the cleaning apparatus is configured to discharge the reactive gas from the cleaning chamber to the drain.

2. The cleaning apparatus of claim 1, further comprising a controller configured to control a cleaning program in the cleaning apparatus, wherein the articles are acted on by the cleaning fluid in a cleaning program step, and wherein the articles are acted on by the reactive gas in a disinfection step.

3. The cleaning apparatus of claim 2, wherein the articles are acted on by the reactive gas in the at least one disinfection step after the cleaning program step has been carried out.

4. The cleaning apparatus of claim 1, further comprising at least one preparation apparatus, wherein the cleaning apparatus is configured to convey the reactive gas, after contact with the articles, through the at least one preparation apparatus.

5. The cleaning apparatus of claim 4, wherein the preparation apparatus comprises one or both of at least one filter and at least one catalyst.

6. The cleaning apparatus of claim 1, further comprising a pressure apparatus configured to generate one or both of an overpressure and a negative pressure in at least part of the cleaning apparatus, wherein the pressure apparatus is designed to divert the reactive gas, after contact with at least part of the cleaning apparatus, into the drain.

7. The cleaning apparatus of claim 1, wherein the plasma source is formed such that the reactive gas is brought into contact with at least part of the fluid source.

8. The cleaning apparatus of claim 1, wherein the plasma source is arranged inside the cleaning chamber and is configured to ignite the plasma inside the cleaning chamber.

9. The cleaning apparatus of claim 1, wherein the reactive gas comprises a plasma.

10. The cleaning apparatus of claim 9, wherein the plasma is a cold plasma having a temperature of less than 100° C.

11. The cleaning apparatus of claim 9, wherein the plasma is a cold plasma having a temperature of less than 80° C.

12. The cleaning apparatus of claim 9, wherein the plasma is a cold plasma having a temperature of less than 60° C.

13. The cleaning apparatus of claim 1, wherein the reactive gas comprises at least one compound which can be generated by the plasma, selected from the group consisting of: ozone, atomic oxygen, atomic nitrogen, and hydrogen peroxide.

14. The cleaning apparatus of claim 1, wherein the care utensils are suitable for receiving human excretions of at least 500 ml.

15. The cleaning apparatus of claim 1, wherein the drain is configured to dispose excretions contained in the care utensils with liquid volumes of at least 500 ml.

16. The cleaning apparatus of claim 1, wherein the odor trap comprises at least one siphon bend.

17. The cleaning apparatus of claim 1, wherein the drain has a diameter or equivalent diameter of at least 30 mm.

18. The cleaning apparatus as claimed in claim 1, wherein the drain has a diameter or equivalent diameter of at least 50 mm.

19. A method for cleaning articles using the cleaning apparatus according to claim 1, wherein the articles are acted on in a cleaning chamber by a cleaning fluid, further wherein, a plasma is ignited in a gas by means of a plasma source and a reactive gas is generated, wherein the reactive gas is brought into contact with the articles.

20. The method of claim 19, wherein the articles comprise care utensils.

21. The cleaning apparatus of claim 1, wherein the plasma source is arranged outside the cleaning chamber, and the cleaning apparatus is configured to convey the reactive gas into at least part of the cleaning chamber.

22. The cleaning apparatus of claim 21, further comprising a fan, a suction apparatus or an overpressure apparatus, wherein the cleaning apparatus is configured to convey the reactive gas into at least part of the cleaning chamber by means of the fan, the suction apparatus or the overpressure apparatus.

* * * * *